United States Patent [19]

Twerenbold

[11] Patent Number: 5,640,010
[45] Date of Patent: Jun. 17, 1997

[54] MASS SPECTROMETER FOR MACROMOLECULES WITH CRYOGENIC PARTICLE DETECTORS

[76] Inventor: Damian Twerenbold, Case Postale 120, CH-2017 Boundry, Switzerland

[21] Appl. No.: 438,707

[22] Filed: May 11, 1995

[30]   Foreign Application Priority Data

Aug. 4, 1994 [CH]  Switzerland .................. 02424/94

[51] Int. Cl.$^6$ ...................................................... H01J 49/40
[52] U.S. Cl. ...................... 250/281; 250/397; 250/396 R
[58] Field of Search .................................. 250/281, 282, 250/397, 396 R, 515.1

[56]   References Cited

U.S. PATENT DOCUMENTS 4,375,033  2/1983  Bjorkholm et al. .................. 250/251

FOREIGN PATENT DOCUMENTS 0360676  7/1989  European Pat. Off. ..

OTHER PUBLICATIONS

*Correlation Measurements of Ionizing Radiation Induced Phonons In Silicon Using Superconducting Tunneling Junctions*, Decoulon et al., Nuclear Inst. and Methods in Physics Research A 294 (1990) 259–267.

*Superconducting Resonator and a Cryogenic GaAs Field–Effect Transistor Amplifier As a Single–Ion Detection System*, Jefferts et al., Review of Scientific Instruments 64 (1993) Mar., No. 3, New York, US.

Anal. Chem., M. Barber et al., 54 (1982) 645 A "Fast Atom Bombardment Mass Spectrometry".

Rapid Comun. Mass Spectrom., J.E. Bruce et al., 7 (1993) 914 "Selected–ion accumulation from an external electrospray ionization Source with a fourier–transform ion cyclotron resonance mass spectrometer".

Anal. Chem., S.M. Michael, 65 (1993) 2614 "Detection of electrospray ionization using a quadrupole ion trap storage/rejection time of flight mass spectrometer".

Anal. Chem., M. Karas and F. Hillenkamp, 60 (1988) 2299 "Laser Desorption Ionization of Proteins with Molecular Masses Exceeding 10, 000 Paltons".

Int. J. Mass Spectrom. Ion Process, R.T. Melver et al., 132 (1994) L1 "FTMS Method for Higher Resolution Matrix Assisted Laser Desorption".

(List continued on next page.)

*Primary Examiner*—Jack I. Berman
*Assistant Examiner*—Kiet T. Nguyen
*Attorney, Agent, or Firm*—Reising, Ethington, Barnard & Perry

[57]  ABSTRACT

A mass spectrometer with phonon sensitive cryogenic particle detector determines the masses of macromolecules, proteins, large peptides, long DNA-fragments and polymers. The kinetic energy of the electrostatically accelerated charged macromolecule is absorbed in the cryogenic particle detector thereby exciting phonons which are detected by phonon sensors. The macromolecules are detected in the single particle counting mode with a sensitivity independent of their respective masses. The mass spectrometer contains a single-channel cryogenic particle detector providing high sensitivity. The mass spectrometer contains a spatially resolving multi-channel cryogenic detector array providing both high sensitivity and high throughput. The mass spectrometer consists of a vacuum vessel in which is a magnet, a mass separator, a feed through and a phonon sensitive cryogenic detector array. The cryogenic detector array consists of an absorber and a specified number of phonon sensors. The mass separator is placed in the magnetic field of the magnet and the feed through, on electrical potential U1, but electrically insulated from the magnet. The cryogenic detector array is on electrical ground potential U2. The macromolecules are accelerated by the voltage difference U1–U2 and reach the cryogenic detector array with a kinetic energy proportional to U1–U2. The cryogenic detector array is cooled to its operating temperature T2 by being thermally mounted to a cold finger of the cryostat with bath temperature T2. The mass of the macromolecule is determined by the spatial and time information provided by the cryogenic detector array.

42 Claims, 16 Drawing Sheets

OTHER PUBLICATIONS

Proc. Natl. Acad. Sci. U.S.A., D.F. Hunt et al., 83 (1986) 6233 "Protein Sequencing by tandem Mass Spectrometry".

Rapid Commun. Mass Spectrom., K.J. Wu et al., 7 (1993) 142 "Matrix–Assisted Laser Desorption TOF MS of Oligonucleotides using 3–Hydroxypicolinic Acid as an Ultraviolet–Sensitive Matrix".

Int. J. Mass Spectrom. Ion Processes, P. Williams, 131 (1994) 335 "TOF MS of DNA Laser–Ablated from frozen Aqueous Solution Application to the Human Genome Project".

Proc. Natl. Acad. Sci. U.S.A., D.F. Hunt et al., 83 (1986) 6233 "Protein Sequencing by tandem Mass Spectrometry".

Science, A.L. Cox et al., 264 (1994) 716 "Identification of a Peptide recognized by five Melanoma–Specific human Cytotoxic T Cell Lines".

Phys. Rev., J. Linhard and M. Scharf, 124 (1961) 128 "Energy Dissipation by Ions in the Kev region".

Annu. Rev. Biophys. Biomol. Struct., M.W. Senko and F.W. McLafferty 23 (1994) 763 "Mass–Spectrometry of Macromolecules: Has its time now Come".

Science, Q. Xie, 256 (1992) 225 "Cloning and Characterization of Inducible Oxide Synthase from Mouse Macrophages".

Advances in DNA Sequencing Technology, R.A. Keller (ed.), SPIE 1891, (1993).

Cell, D.C. Schwartz and C.R. Cantor, 37 (1984) 67 "Separation of Yeast Chromosome–Sized DNAS by Pulsed Field Gradient Gel Electrophoresis".

Methods in Molecular Biology, vol. 12, "Pulsed–Field Gel Electrophoresis", M. Burmeister and L. Ulanovsky (ed.) (1992).

Europhys. Lett., D. Twerenbold, 1 (1986) 209 "Giaever–type Superconducting Tunneling Functions as High–Resolution X–ray Detectors".

Europhys. Lett., H. Kraus etal. (1986) 161 "High–Resolution X–ray Detection with Superconducting Tunnel Functions".

Proceedings of the 5 International Workshop on Low Temperature Detectors, University of California at Berkeley, Jul. 29–Aug. 3, 1993. Special issue: *Journal of Low Temperature Physics* 93 (1993).

Phys. Rev B., D. Twerenbold, 34 (1986) 7748 "Nonequilibrium Model of the Superconducting Tunneling Function X–ray Detector".

Appl. Phys. Lett., N.E. Booth, 50 (1987) 293 "Quasiparticle Trapping and the Quasiparticle Multiplier".

*Advanced Detectors For Mass Spectrometry*, Human Genome 1991–92 Program Report, Department of Energy, Joseph M. Jaklevic et al., Published Jun. 1992.

MASS SPECTROMETER FOR MACROMOLECULES WITH CRYOGENIC PARTICLE DETECTORS

BACKGROUND OF THE INVENTION

This invention relates to a mass spectrometer for macromolecules.

In prior art mass spectrometry, various techniques have successfully been established to volatilize and ionize biological macromolecules: Fast Atom Bombardment (FAB) [1], Electro Spray Ionization (ESI) [2, 3] and Matrix Assisted Laser Desorption/Ionization (MALDI) [4, 5, 6, 7]. In the MALDI method, the macromolecules are embeded with low concentration in a matrix of material with high photon absorption. When illuminated with high intensity laser light, the matrix heats up rapidly and evaporates into a plasma. During evaporation momentum is transferred to the macromoleculs which are subsequently ionized in the plasma. Because the matrix plasma cools rapidly, most macromolecules remain intact. In prior art mass spectrometers the masses of those ionized macromolecules are determined with the time-of-flight (TOF) method [3, 7, 8], with the Fourier Transform Ion Cyclotron Resonance (FT-ICR) method [2, 5, 6] or with the single or multi quadrupol mass filter method [9, 10].

The disadvantage of prior art ionizing particle detectors used in mass spectrometers for macromolecules is the strong decrease of ionization efficiency for massive macromolecules owing to their decreasing particle velocities [11, 12]. In state of the art detectors for mass spectrometry, the accelerated macromolecule emits an electron on impact with the detector which is subsequently multiplied by electron multiplier techniques. The efficiency to emit said first electron depends on the velocity of the impacting particle [11] which for a massive macromolecule is small. This lack of detector efficiency can be compensated for in prior art mass spectrometers by increasing the flux of macromolecules, however by the expense of decreasing the overall system sensitivity. Generally, in prior art mass spectrometers the detection of macromolecules with masses larger than typically 50000 amu is inefficient. With the FT-ICR technique much larger masses can be detected, however, at the expense of large integration times of the order of one second, excluding applications where high throughput is required.

Mass spectrometry is used in biology for protein sequencing [9, 13] and protein identification [10] by measuring the mass distribution of protein-fragments. It is also considered to be a promising technique to increase the speed and to reduce the cost in DNA-sequencing [2, 3, 5, 6, 7, 8, 14]. The standard DNA-sequencing procedure is to separate an aliquot of DNA-fragments, prepared according to the Maxam-Gilbert and Sanger strategy, using the pulsed gel-electrophoresis technique [15, 16]. In this technique, the DNA-fragments are separated by their lengths according to their migration properties in a gel to which an electrical field is applied. The spatially separated bands of DNA-fragments are conventionally recorded by auto-radiography and fluorescent techniques.

The disadvantage of said gel-electrophoresis technique is the slow sequencing rate and the poor mass resolution for very large DNA-fragments. The disadvantage of prior art mass spectrometers for high rate DNA-sequencing is the low sensitivity of ionizing detectors for DNA-fragments consisting of more than 100 bases, making inaccessible the increase in DNA-sequencing rate which is possible with mass spectrometry.

SUMMARY OF THE INVENTION

Accordingly, it is an object of this invention to provide a novel mass spectrometer for massive macromolecules.

It is a still further object of the invention to provide novel apparatus for measuring the masses of macromolecules with a detection efficiency independent of mass, i.e. allowing also the measurement of macromolecules with very high mass.

It is a still further object of the invention to provide novel apparatus for measuring the masses of macromolecules in the single particle counting mode.

It is a still further object of the invention to provide novel apparatus for measuring the masses of macromolecules with a detector system having both high temporal and high spatial resolution.

It is a still further object of the invention to provide novel apparatus for high throughput and high sensitivity base sequencing of short and long DNA-fragments.

It is a still further object of the invention to provide novel apparatus for high throughput and high sensitivity amino acid sequencing of small and large proteins.

It is a still further object of the invention to provide novel apparatus for high throughput and high sensitivity identification of small and large proteins.

It is a still further object of the invention to provide novel apparatus for high throughput and high sensitivity identification of small and large polymers.

Those objects are achieved by using phonon sensitive cryogenic particle detectors. In cryogenic particle detectors, the absorbed kinetic energy of the impacting accelerated macromolecules is converted into phonons (i.e. vibrations of the solid state lattice of the detector) which are converted into an electronic signal by phonon sensors. Said phonon sensors are sensitive only at cryogenic temperatures (i.e. temperatures less than a few Kelvin) where the background of thermal phonons is negligable.

In accordance with the above and further objectives of the invention, one embodiment of apparatus is a time-of-flight mass spectrometer where the macromolecules are separated by their mass dependent velocities which is proportional to $\sqrt{m}$, where m denotes the mass of the macromolecule. For the same emission time, heavier macromolecules arrive later at the position of the detector than corresponding lighter macromolecules. Said cryogenic particle detectors determine the arrival time of a macromolecule in the single particle counting mode with a sensitivity independent of mass, as it is the absorbed kinetic energy of the macromolecule which determines the efficiency of said detector, and not the velocity. The kinetic energy is for all said accelerated macromolecules the same.

In another embodiment, single or multiple quadrupole mass spectrometers separate and analyse the masses of macromolecules by quadrupole mass filters where cryogenic particle detectors measure the emerging macromolecules. Very low quantities of macromolecules are required in this embodiment because of the single particle counting mode of said cryogenic particle detector.

In another embodiment, macromolecules are spatially separated by a stationary magnetic field according to their mass-to-charge ratio, subsequentialy accelerated and then detected by spatial resolving cryogenic particle detectors.

In another embodiment, macromolecules are desorbed in a pulsed time sequence, spatially separated by a stationary magnetic field according to their mass-to-charge ratio, subsequentialy accelerated and then detected by spatial and temporal resolving cryogenic particle detectors. From the spatial and temporal information of the macromolecule event, and the known emission structure, the emission time of the macromolecule can be reconstructed and the mass determined from the time-of-flight. This leads to a parallel operating time-of-flight mass spectrometer with high sensitivity and throughput.

In accordance with the above and further objectives of the invention, one embodiment of said cryogenic particle detector is using crystal substrates as absorbers and superconducting tunneling junctions operated in the Giaever-mode as said phonon sensors.

In another embodiment of said cryogenic particle detector, the Giaever-type superconducting tunneling junctions are used both as absorbers and phonon sensors.

In another embodiment of said cryogenic particle detector, the phonon sensitivity of said Giaever-type superconducting tunneling junctions is enhanced by depositing said superconducting tunneling junctions on top of large area superconducting films which have a superconducting energy gap larger than the corresponding films of said superconducting tunneling junctions in order to use the quasiparticle trapping effect.

In another embodiment of said cryogenic particle detector, the crystal absorber is covered with superconducting transition edge phonon sensors.

In another embodiment of said cryogenic particle detector, microcalorimeters are used with consist of crystal absorber of low heat capacitance and high sensitivity thermistors as phonon sensors.

In another embodiment of said cryogenic particle detector, microcalorimeters are used with consist of crystal absorber of low heat capacitance and high sensitivity kinetic conductance thermometers as phonon sensors.

In another embodiment of said cryogenic particle detector, microcalorimeters are used where the crystal absorber and the thermal phonon sensor are identical.

In another embodiment of said cryogenic particle detector, the crystal absorber is covered with superconducting granules in the superheated phase which act as phonon sensors.

In another embodiment of said cryogenic particle detector, superconducting granules in the superheated phase are used both as absorbers and phonon sensors.

From the above summary, it can be understood that mass spectrometer of this invention has several advantages: (1) it allows the mass determination of a macromolecule with a sensitivity independent of the mass of the macromolecule, i.e. also for very massive macromolecules; (2) it allows the mass determination of a macromolecule in the single particle counting mode, i.e. enabling very high sensitivity; (3) the thin film technology for producing said phonon sensors allows for cryogenic detector array with high spatial resolution, i.e. high throughput is possible by spatially splitting the macromolecule beam and performing parallel measurements in time; (4) the sensitivity and throughput of DNA-sequencing can be improved by several orders of magnitude; (5) the sensitivity and throughput of protein-sequencing can be improved by several orders of magnitude; (6) the sensitivity and throughput of protein-identification can be improved by several orders of magnitude; (7) the sensitivity and throughput of polymer- identification can be improved by several orders of magnitude.

SUMMARY OF THE DRAWINGS

The above noted and other features of the invention will be understood from the following detailed description when considered with reference to the accompanying drawings in which:

FIG. 8 or FIG. 9 used in the emobodiment of FIG. 11;

DETAILED DESCRIPTION

Figure 1:
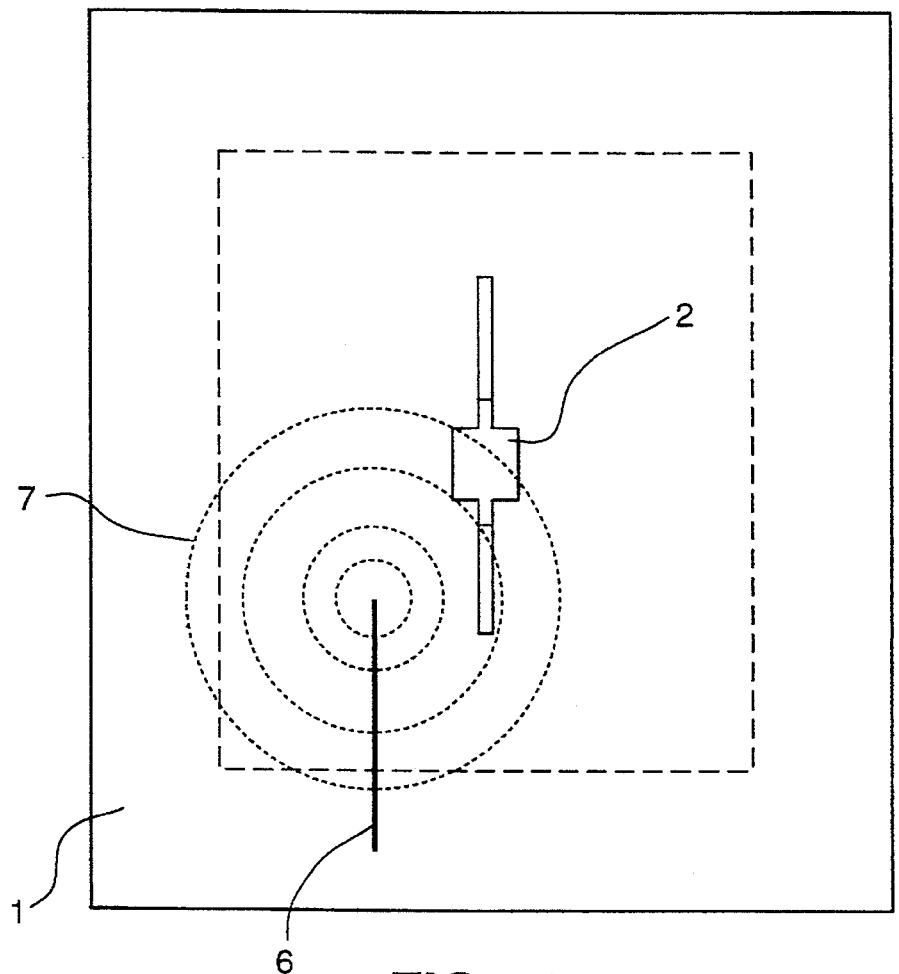
FIGS. 1 and 1A are a schematic of an embodiment of a phonon sensitive cryogenic detector.
Figure 1A:
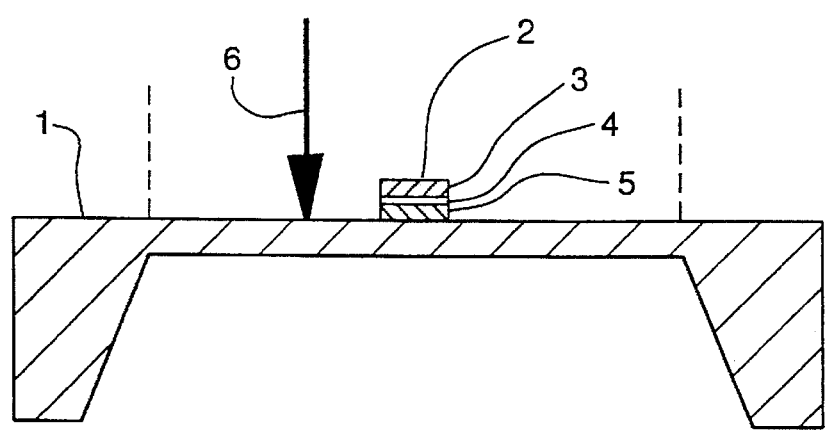

The schematic cryogenic particle detector shown in FIGS. 1 and 1A consist of an absorber, indicated by the reference numeral 1, onto which a phonon sensor 2 is deposited. In the embodiment shown in FIGS. 1 and 1A, this phonon sensor is a superconducting tunneling junction consisting of a top film 3 of a few 100 nm separated by a thin oxide barrier 4 of a few nm and a bottom film 5 of a few 100 nm. Superconducting tunneling junctions are well established as α-particle and x-ray detectors [17, 18, 19] and the physics is well understood [20]. Other embodiments of cryogenic phonon sensors are (see reference [19]): superconducting transition edge thermometers close to $T_c$, semiconducting thermistors, superconducting kinetic inductance thermometers and superheated superconducting granules and dots. Basically the only requirement for the phonon sensor is to be sensitive to energy depositions of a few 10 keV and to have rise times not larger than 100 nsec. Cryogenic particle detectors operate at temperatures below a few Kelvin, where the background of thermally excited phonons is negligable. The operating principle of a phonon sensitive cryogenic particle detector for the mass spectrometry of macromolecules is the following (see FIGS. 1 and 1A): a macromolecule 6 which has been accelerated to a kinetic energy of typically a few 10 keV by the electric field in the mass spectrometer produces phonons 7 which propagate through the absorber 1 and are eventually converted in the phonon sensor 2 into an electric signal. The sensitivity of phonon sensitive cryogenic particle detectors to the absorption of ionizing particles with an energy of a few keV has been demonstrated by [21] and by other authors (see references in [19]). The novelty of this invention is the implementation of cryogenic particle detectors in a mass spectrometer for massive macromolecules. Cryogenic particle detectors, as shown in the emobodiment of FIGS. 1 and 1A, have the unique property that they do not only detect ionizing particles, but that they are equally or more sensitive to the nonionizing direct transfer of kinetic energy to the lattice of the absorber. In said embodiment shown in FIGS. 1 and 1A, the phonon collection efficiency is enhanced by etching down the substrate, e.g. single crystal silicon, to a thickness of a few 10 µm in order to localize the non-thermal phonon density in the vicinity of the phonon sensor.

Figure 2:
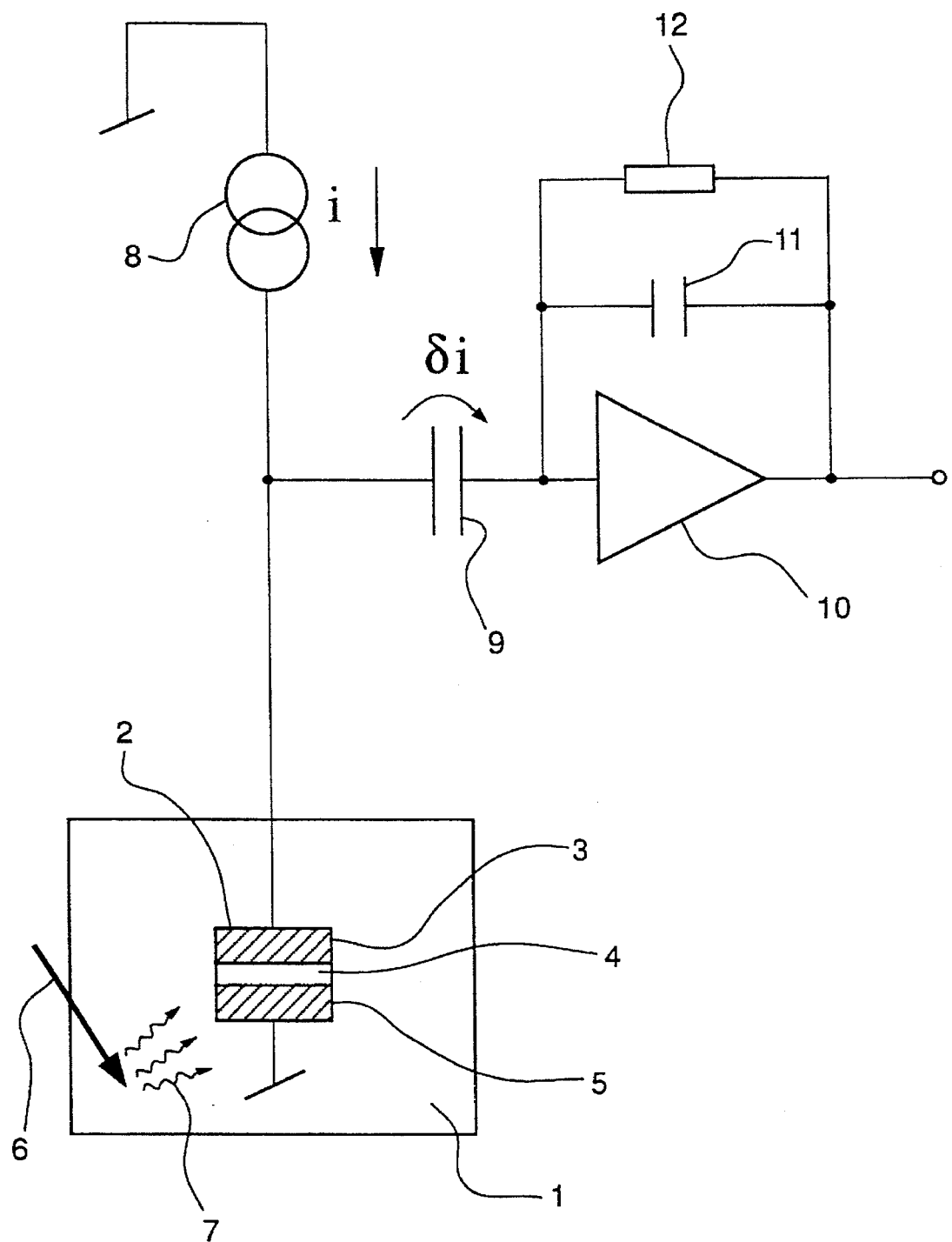
FIG. 2 shows a schematic of the electronic circuitry of the embodiment shown in FIGS. 1 and 1A.

In FIG. 2 the electronic read circuitry is shown in the case of the embodiment of a superconducting tunneling junction as a phonon sensor: The phonons 7 produced by the abosorption of a macromolecule 6 propagate through the absorber 1 of which some enter the superconducting films 3 and 5. There, the phonons which energy larger than the Cooper pair binding energy 2Δ break Cooper pairs (the coherent electronic bound states in a superconductor) and produce excess quaisparticles (the electronic single excitation states in a superconductor). The two superconducting films 3 and 5 are at different energy potentials owing to the biasing current i which is provided by the current source 8. A net current of excess quasiparticles then tunnels across the insulating barrier 4 (the tunneling of Cooper pairs, the DC Josephson current, is prohibited by a magnetic field applied parallel to the insulating barrier). As the phonons 7 and the corresponding excited excess quasiparticles decay on the time scale of a few µsec, the excess quasiparticle curret δi is of transient nature and will flow through the capacitor 9. With a charge sensitive preamplifier consisting of a suitable operation amplifier 10, a feed back capacitor 11 and a feed back resistor 12 the excess quasiparticle current δi is integrated and the integrated charge will be proportional to the number of phonons 7 absorbed in the phonon sensor 2. Macromolecules can of course also be absorbed in the phonon sensor itself and produce directly a signal, which is an alternative embodiment of said cryogenic particle detector.

Figure 3:
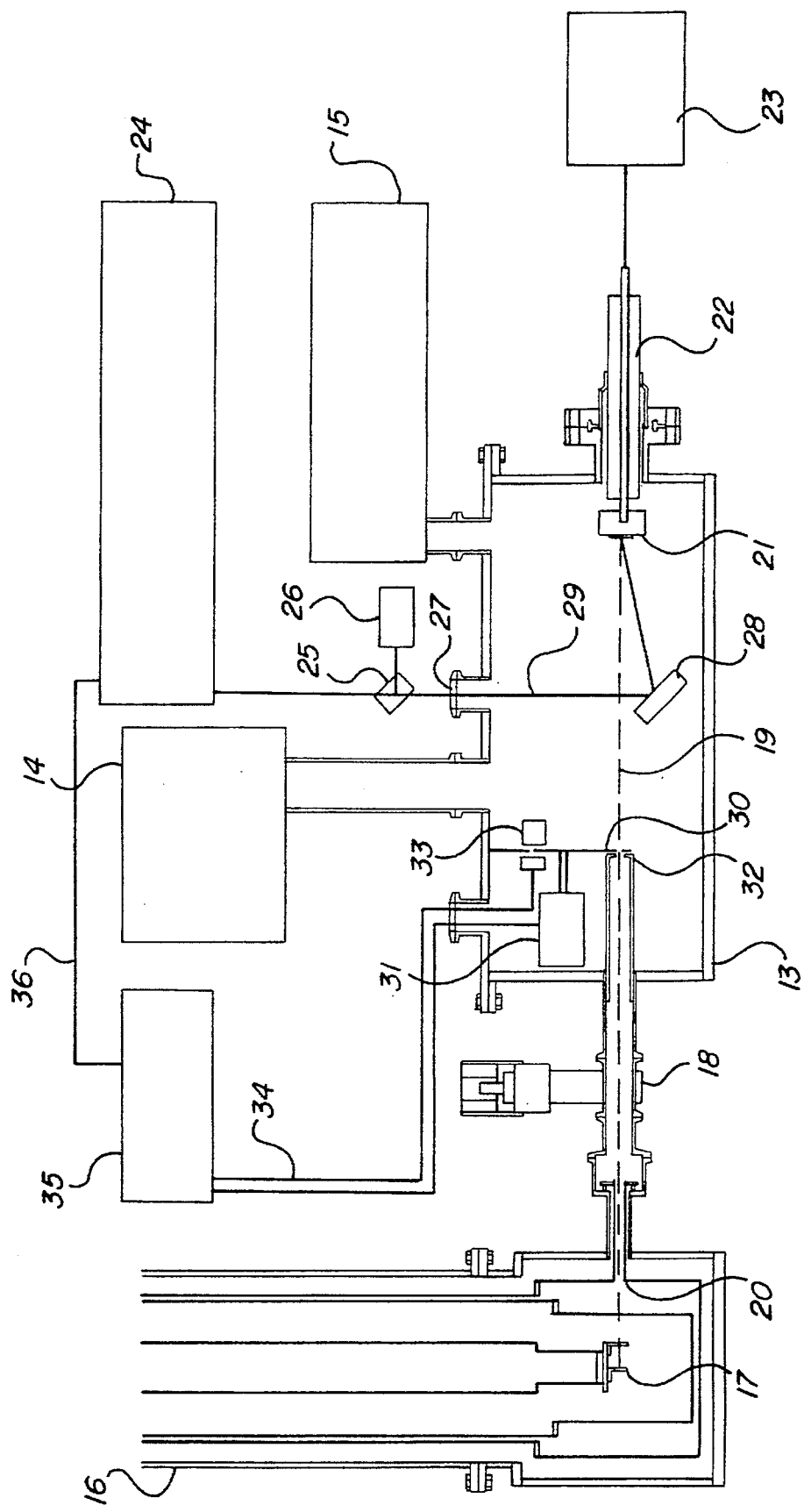
FIG. 3 is a schematic of an embodiment of the invention using a single channel cryogenic detector as detector in a MALDI-TOF mass spectrometer.

FIG. 3 shows a an embodiment of a mass spectrometer for macromolecules with cryogenic particle detectors using a setup generally referred to as a MALDI-TOF (matrix assisted laser desorption/ionization time of flight). A vacuum vessel 13 is evacuated by a turbo pump system 14 to a vacuum of about $10^{-5}$ mbar which is monitored by a vacuum measurement system 15. A cryostat 16 with the cryogenic particle detector 17 attached to the cold finger is connected to the vacuum vessel 13 via a valve 18. The beam of macromolecules 19 produced in the vacuum vessel 13 enters the cold area of the cryostat 16 by a series of small holes 20 in the cold shields of the cryostat. The beam of macromolecules 19 is produced by mounting the macromolecule sample 21 on a high voltage feed through 22 which is connected to a high voltage power supply 23 and by illuminating the sample with a laser beam 29 from a laser source 24. The laser can be an UV-laser or an infrared laser. The laser beam 29 emerging from the laser source 24 is split in a beam splitter 25: one part of the beam is used to measure the laser power in a power meter 26 and the other part enters the vacuum vessel 13 via the window 27. In the vacuum vessel, the laser beam 29 is directed to the sample 21 via a mirror 28. The probe consists of a light-sensitive matrix solution (e.g. sinapinic acid or α-cyano-4-hydroxycinnamic acid [12]) into which the macromolecules have been diluted in ratios exceeding $10^4:1$. The laser power, typically a few mJ in a few nsec, is abosorbed by the matrix, which explodes and turns into an electric plasma. The expanding matrix transfers momentum to the macromolecules which are thus volatilized and subsequently charged by the plasma character of the expanding matrix. Owing to the electric field in the vacuum vessel produced by the high voltage on 22, the macromolecules with the same charge as the high voltage potential will be accelerated towards the transfer tube 32 into the cryostat 16, through the holes of the cooling shields 20 and finally onto the cryogenic detector 17. The time difference of the laser trigger and the time of arrival signal of the cryogenic particle detector is a measure for the mass of the macromolecule. As the cryogenic particle detector is a very sensitive device, no light and no low mass debris from the matrix should hit the detector, which most probably would lead to a saturation of the detector and/or heating up of the cryostat. In order to prevent this a mechanical shutter 30 is operated in front of the transfer tube 32. In one embodiment of the shutter, a motor 31 turns a disk with a slit where a light emitting diode and light detection system 33 measures the position of the slit and an electronic control system 35 gives an appropriate trigger signal 36 to the laser 24.

Figure 4:
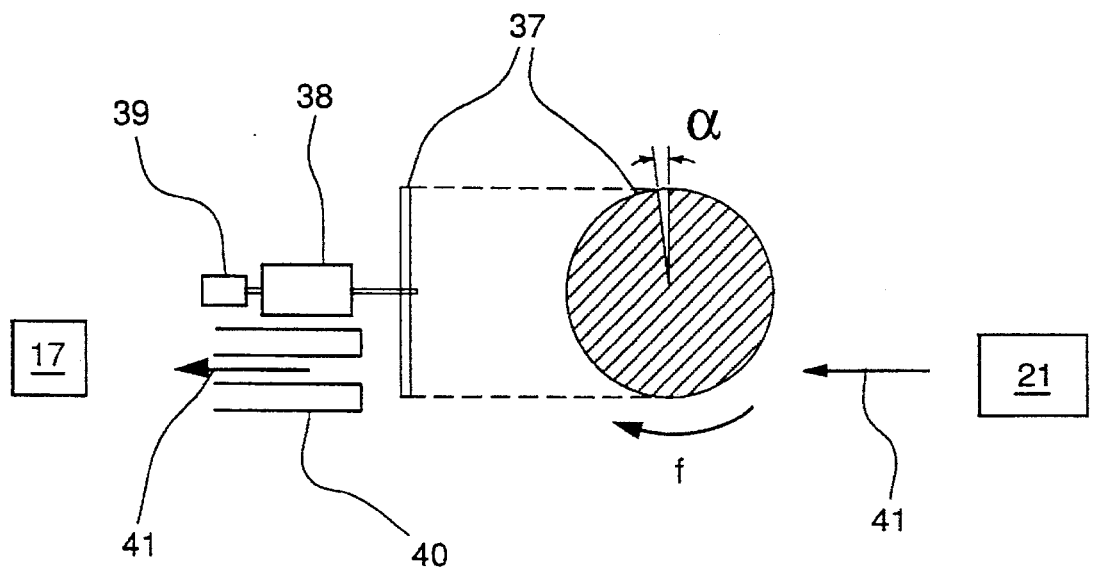
FIG. 4 is a schematic showing an embodiment of the mechanical shutter for the MALDI-TOF shown in FIG. 3.
Figure 5:
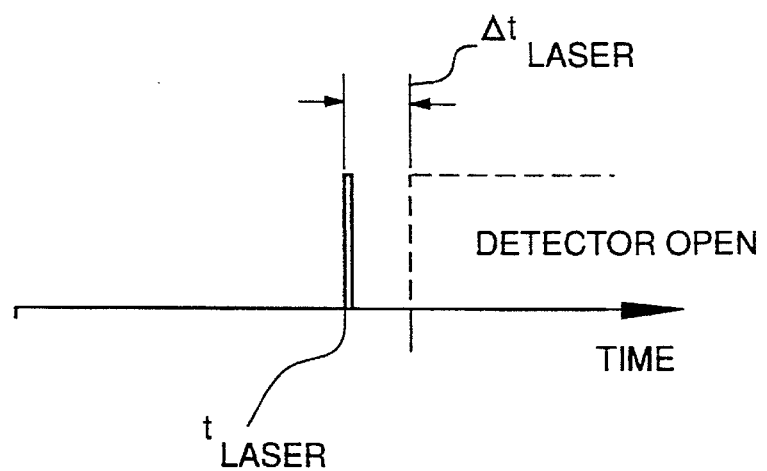
FIG. 5 illustrates the timing of the laser trigger and the shutter shown in FIG. 4.
Figure 6:
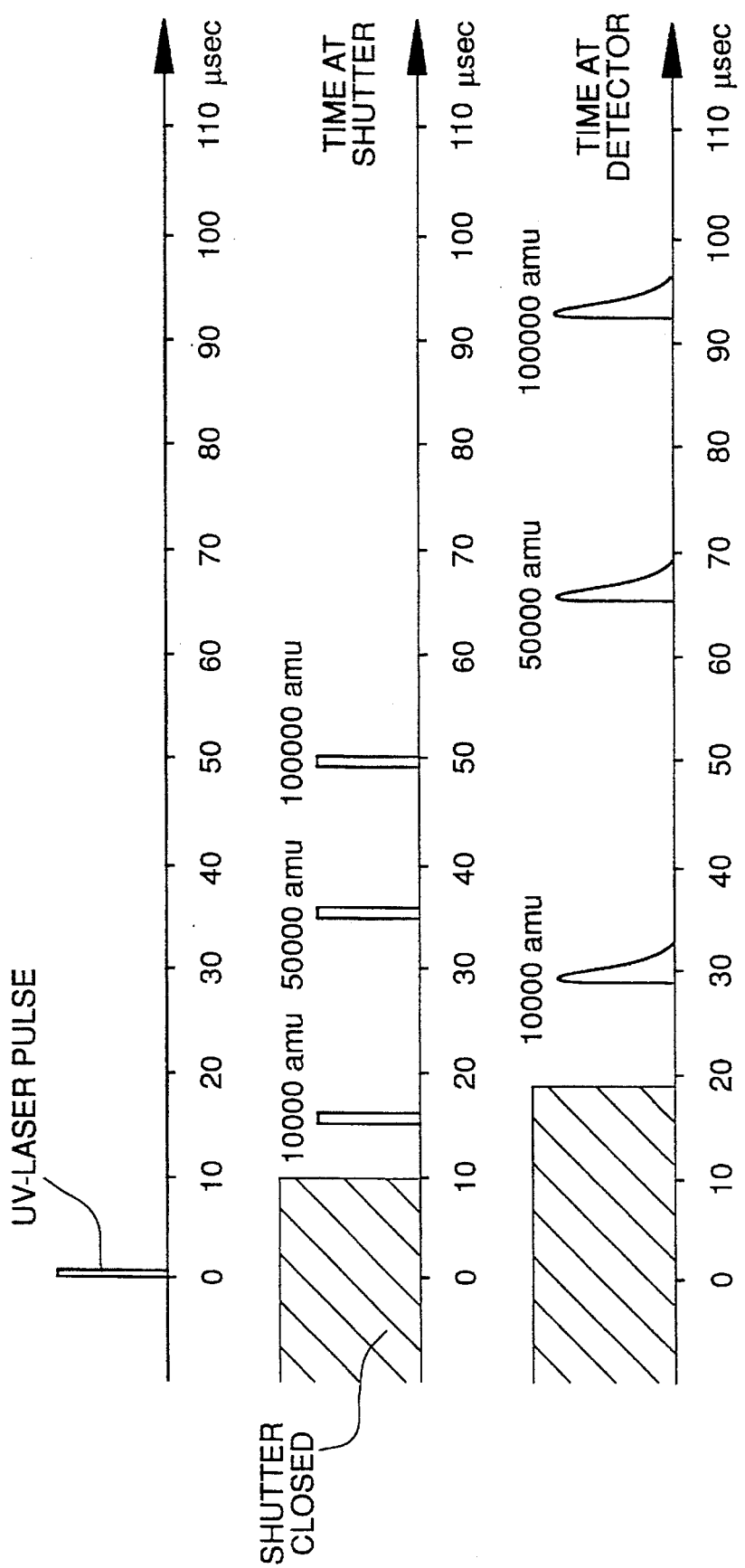
FIG. 6 illustrates the timing of events for three macromolecule masses for the embodiment shown in FIG. 3 and FIG. 4.

In FIG. 4, a particular embodiment of this mechanical shutter is shown: a motor 38 turns a disk 37 with a slit of opening α (typically 5° to 10°) at a frequency f (typically between 50 and 100 Hz). The position of the rotating shaft is monitored by an incremental decoder 39. Accelerated macromolecules 41 from the source 21 will enter the tube 40 connecting the vacuum vessel to the cryostat only when the slit of 37 is at the position of the tube. By suitable choice of the timing of the laser trigger, the beam 41 of macromolecule hitting the cryogenic particle detector 17 will consist only of macromolecules with masses larger than a certain cutoff value. As is shown in FIG. 5, the electronic control system of the mechanical shutter will be such that a trigger signal $t_{laser}$ will be transmitted to the laser a specified time interval $\Delta t_{laser}$ prior to the opening of the shutter 37 at the position of the transfer tube 40. The detector is then exposed to a specified mass range of macromolecules depending on the angle α of the opening of the slit and the rotating speed f of the shutter. In FIG. 6, the arrival times of macromolecules with different masses is shown at the position of the rotating mechanical shutter and at the position of the detector for the embodiment shown in FIG. 3. Because the kinetic energy is proportional to $mv^2$, where m is the mass and v the velocity of the macromolecule, the time-of-flight is proportional to $\sqrt{m}$. The shaded area at times prior to 10 μsec in this example corresponds to the mass range of macromolecules which does not reach the detector.

In order to improve the throughout, another embodiment of the invention uses cryogenic detector arrays which resolve both the time of impact and the position of impact of the accelerated macromolecule on said cryogenic detector array. As many embodiments of cryogenic detectors use thin film deposition and lithography techniques, small scale structuring on the μm level will provide a high spatial resolution of the position of impact. In this preferred embodiment of the invention, macromolecules are separated spatially in a magnetic field by their mass/charge ratio and the mass is determined by the position of impact of the macromolecule on the cryogenic detector array. When, in another version of this embodiment, a pulsed emission technique is used, the mass spectrometer is a highly parallel time-of-flight mass spectrometer, allowing the simultaneous determination of a large range of masses in the short succession of a few μsec. This embodiment of the mass spectrometer will be discussed in detail below. First some embodiments of the cryogenic detector arrays will be presented.

Figure 7:
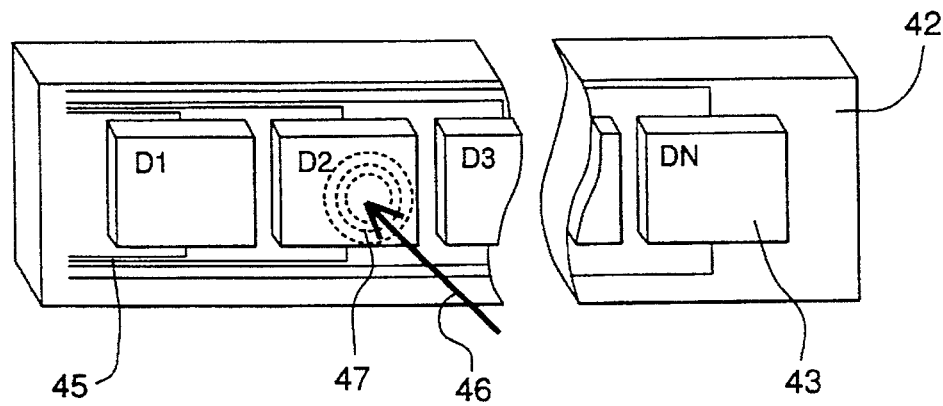
FIG. 7 is a schematic of an embodiment of a spatial resolving cryogenic detector array where the macromolecules are absorbed directly in the phonon sensor.
Figure 8:
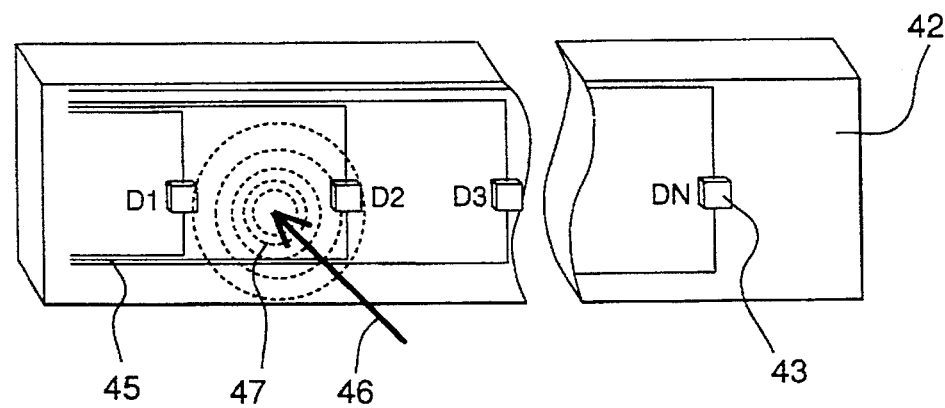
FIG. 8 is a schematic of an alternative embodiment of a spatial resolving cryogenic detector array where the macromolecules are absorbed in the substrate and are sensed indirectly in the phonon sensor.
Figure 9:
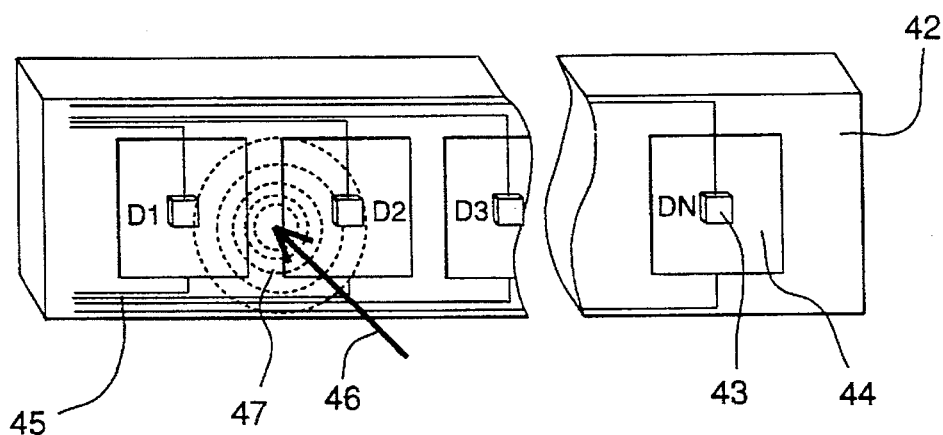
FIG. 9 is a schematic of an alternative embodiment of FIG. 8 where the phonon sensors are superconducting tunneling junctions with quasiparticle trapping films.

The cryogenic detector array used in this invention consists of a number N of phonon sensors D1 . . . DN with current leads 45 on a substrate 42 as shown in FIG. 7, FIG. 8 and FIG. 9. In the embodiment of a cryogenic detector array shown in FIG. 7, the accelerated macromolecule 46 is absorbed directly in the phonon sensor 43 where phonons 47 are produced and are turned into an electronic signal directly. The advantage of this embodiment is the high efficiency of phonon-to-charge conversion and the fast timing signal owing to this direct process. However, phonon sensors with large area surface areas are required, which may be technologically difficult to fabricate (at least in the case of superconducting tunneling junctions). An alternative in said embodiment of FIG. 7 would be a large number of phonon sensors with small areas which, however, would lead to a very large number of electronic channels 45.

Therefore, a preferable embodiment of a cryogenic detector array is shown in FIG. 8: the accelerated macromolecule 46 is absorbed in the absorber and the produced phonons 47 propagate through the absorber and are converted into an electronic signal by the phonon sensors 43. When pure single crystals are used as substrates, e.g. single crystal silicon, the phonons can propagate ballistically large distances and will be sensed than more than one phonon sensor. In said embodiment where superconducting tunneling junctions are used as phonon sensors, the electronic signal is proportional to the number of phonons absorbed and the pulse height is proportional to the superconducting tunneling juction's distance to the point of interaction. Hence, a precise determination of this point of macromolecule absorption can be determined by calculating the centroid of the different pulse heights corresponding to the various junctions responding to the phonon pulse. An alternative embodiment of FIG. 8 is shown in FIG. 9 where an additional superconducting film 44 is deposited under the superconducting tunneling junction. The material of this superconducting film is chosen such that its superconducting energy gap Δ is larger than the corresponding gap of the junction, in order for the quasiparticle trapping effect to occur [22]. The quasiparticles produced by the phonons 47 in 44 will propagate via quasiparticle diffusion in 44 and ultimately be trapped in the lower film of the superconducting tunneling junction (see 5 of FIG. 1). There they will tunnel through the oxid barrier and produce the detector signal as described above. The embodiment of FIG. 9 improves the phonon collection efficiency of FIG. 8. Calculations presented below show that the requirements on spatial and temporal resolution of the CDA are technologically reasonable: in the specific model of the embodiment of the invention presented in the following paragraph, a spatial resolution of δx=0.1 mm and a temporal resolution of δt=100 nsec turns out to be sufficient for achieving a mass resolution of 100 amu for a mass of 600000 amu. In those calculation, the cryogenic detector array is 10 cm in length and consists of 100 phonon sensors. Other embodiments of phonon sensors have been mentioned above in the discussion of FIG. 1.

Figure 10:
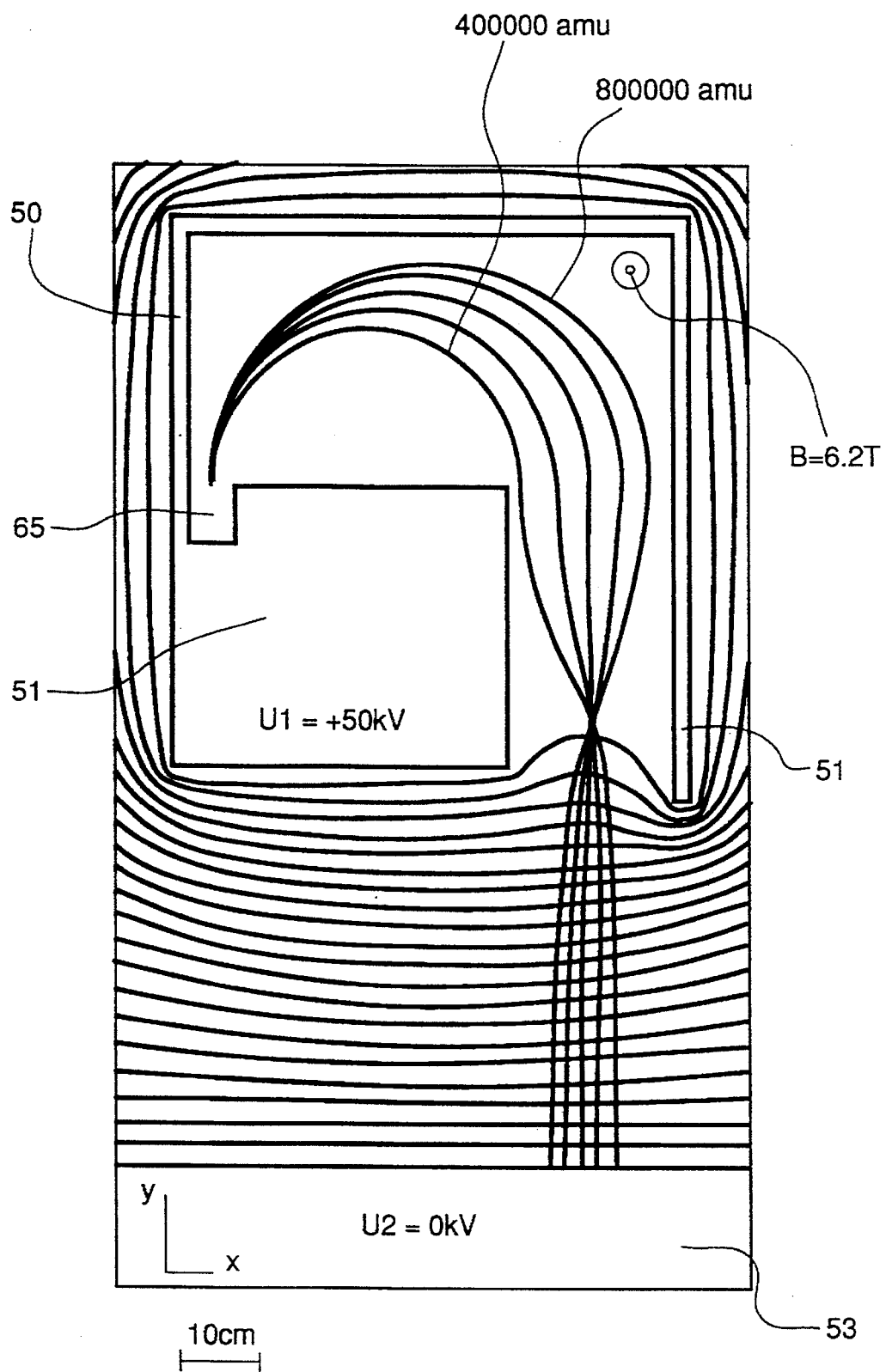
FIG. 10 shows the calculated trajectories of macromolecules of selected masses in an alternative embodiment using cryogenic detector arrays.

With the cryogenic detector arrays presented above, the preferred embodiment of this invention is a mass spectometer with calculated macromolecule trajectories as shown in FIG. 10: macromolecules are volatilized, ionized and pre-accelerated in 51, then separated by their mass/charge ratios in a magnetic field 50, subsequently accelerated electrostatically by the potential difference U1–U2 and detected by the cryogenic detector array 53. There, both the position of impact and the time of impact of the macromolecules are determined by in the single particle counting mode. Again, it should be mentioned that one of the major improvements of this invention is the sensitivity of the cryogenic detector also for high macromolecule masses. In the following, a specific design of the preferred embodiment is presented, and the results of calculations of the corresponding design are discussed. According to those calculations masses of up to $10^6$ amu could be measured with a resolution of 100 amu. In addition, the mass spectrometer can be operated in a quasi-continuos mode with a duty cycle of 10%. Because of the single counting detection mode of the cryogenic detectors, only a small amount of macromolecules would be required, typically considerably less than a femtomol.

Figure 11:
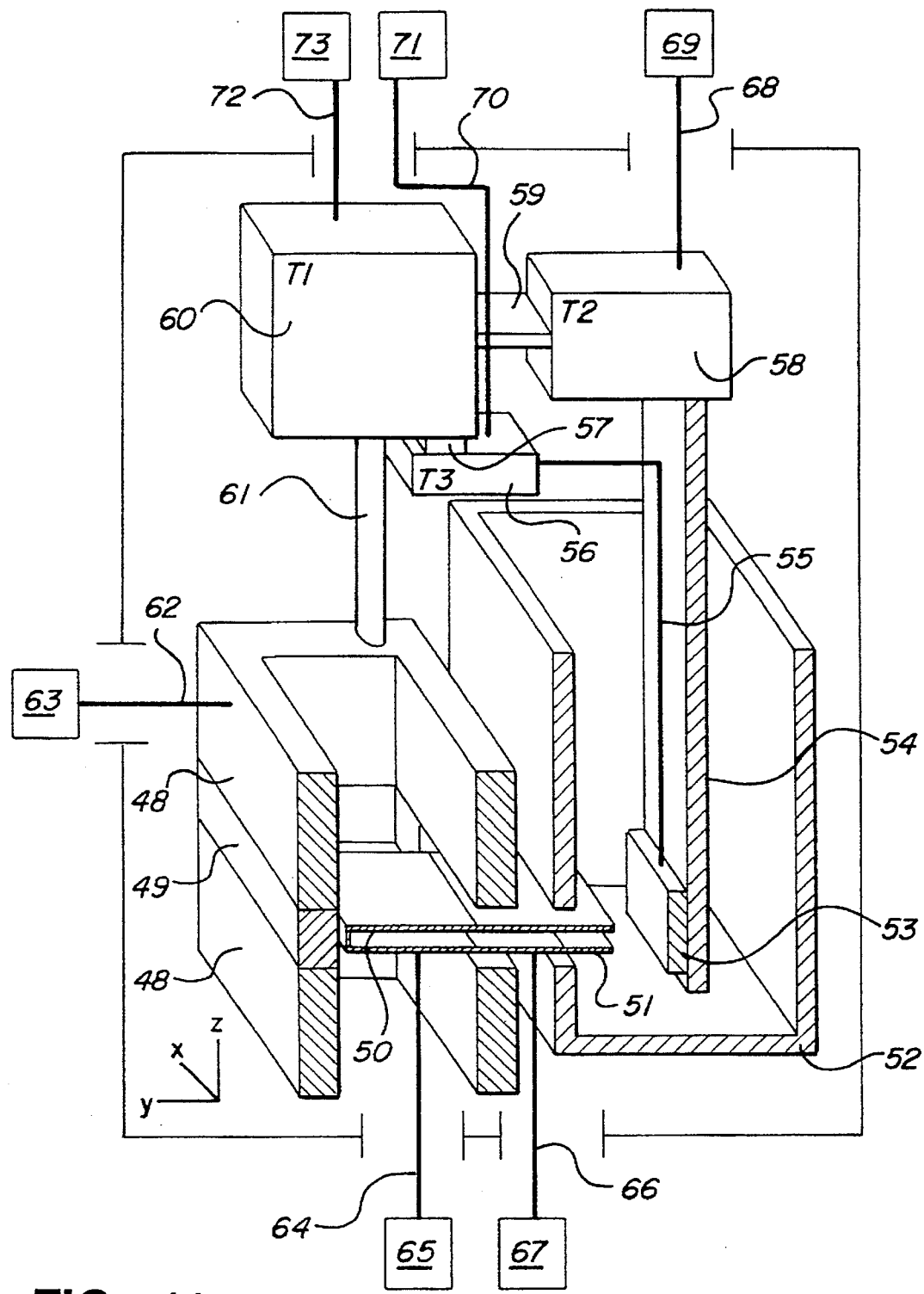
FIG. 11 is a schematic of an embodiment of a mass spectrometer with macromolecule trajectories as shown in FIG. 10, where mass separation of the macromolecules occurs spatially in a magnetic field and the macromolecules are detected by a cryogenic detector array.

The preferred embodiment of the high throughput mass spectrometer with a cryogenic detector array is shown schematically in FIG. 11. The two basic components are: a magnet consisting of two superconduting rectangular Helmholtz coils 48, creating a homogeneous magnetic field B parallel to the z-axis, and a cryogenic detector array 53 inside a superconducting magnetic shield 52. All components are in the same vacuum system and are cooled by a combined cryogenic system 60. T1 is the operating temperature of the superconducting magnet, T2 the operating temperature of the cryogenic detectors which are cooled by an additional cryostat 58, and T3 the operating temperature of the preamplifiers.

The sample to be analyzed is placed in the pre-acceleration chamber 51 where the macromolecules are volatilized and ionized by an external mechanism 67 with feed through 66, e.g. laser beam in the case of MALDI or a capillary in the case of ESI. The ionized macromolecules are pre-accelerated to a kinetic energy of typically a few 100 eV and enter the mass separator 50 which is placed inside of the magnet with a magnetic field of the order of a few Tesla, depending on the selected mass range. Both, pre-acceleration chamber 51 and mass separator are on an electrostatic potential of U1 maintained by a high voltage supply 65 via current lead 64, however, electrically insulated from the magnet. The superconducting magnet consists of two superconducting rectangular Helmholtz coils 48 separated by a spacer 49 of superconducting material for the magnetic field at the position of the mass separator 50 to be as parallel to the z-axis as possible. The magnet is cooled by the cryostat 60 via the thermal contact 61 to its operating temperature T1. Reference number 73 designates the supply of cryogenic liquids and 72 the transfer line 72. The current of the superconducting magnet is supplied by a current source 63 through the leads 62.

In the prependicular magnetic field B of the magnet, the charged macromolecules move on circular paths with a radius of curvature inversely proportional to their masse/charge ratio (see FIG. 10). After describing exactly a half circle, the mass separated macromolecules enter a post-acceleration stage and finally reach the cryogenic detector array 53. The kinetic energy of the macromolecules at the position of the cryogenic detector array is e.(U2–U1), where e is the unit charge, U1 is the electric potential of the mass separtor and U2 the electric potential of the cryogenic detector array which will usually be at ground potential. In order to protect the cryogenic detector array from the strong magnetic stray fields, it is placed in magnetic shielding 52, preferably also of a superconducting material. The cryogenic detector array 53 is connected thermally to the cold finger 54 which is cooled by the cryostat 58 to the operating temperature T2 of the cryogenic detector array 53. The cryostat 58 is connected to the major cryostat 60 for pre-cooling and liquification of $^3$He in the case of an embodiment of 58 as a $^3$He-cryostat. The cryostat is controlled by a temperature controll system and pumps 69 via the connection 68. The cryogenic detector array is biased and read out electronically by an electronic pre-amplifier system 56 which can be cooled to its operating temperature T3 via the thermal link 57 to the cryostat 60. The output of the pre-amplifiers is connected to the data acquisition system 71 via connection 70.

In the following, the response of this high-throughput embodiment of the invention to various design and operating parameters is illustrated by presenting the results of various calculations. Basically, a 2-dimensional computer code has been used [23] which allows the calculation of electric and magnetic fields and the determination of trajectories of macromolecules in those fields. The trajectory calculations yielded both spatial and temporal information of the macromolecule at any given time step. Unless noted otherwise, the parameters of this particular embodiment in the calculation were: geometry as shown in FIG. 10, where the most relevant dimension is the inner dimension of the mass separator 50 (64 cm×32 cm). With those dimensions, and the configuration as shown in FIG. 10, the macromolecule masses between M=40000 amu and M=800000 amu are detected by the cryogenic detector array for a magnetic field B=6.5 Tesla, a pre-accelaration voltage $U_{pre}$=200 V and a post acceleration voltage $U_{post}$=50 kV. The spatial detector resolution is assumed to be δx=0.1 mm and the temporal detector resolution 100 nsec. Both values are typical values for cryogenic particle detectors and are technologically realizable. For calculations where the mass of the macromolecule was fixed, an intermediate value of M=600000 amu was chosen.

Figure 12:
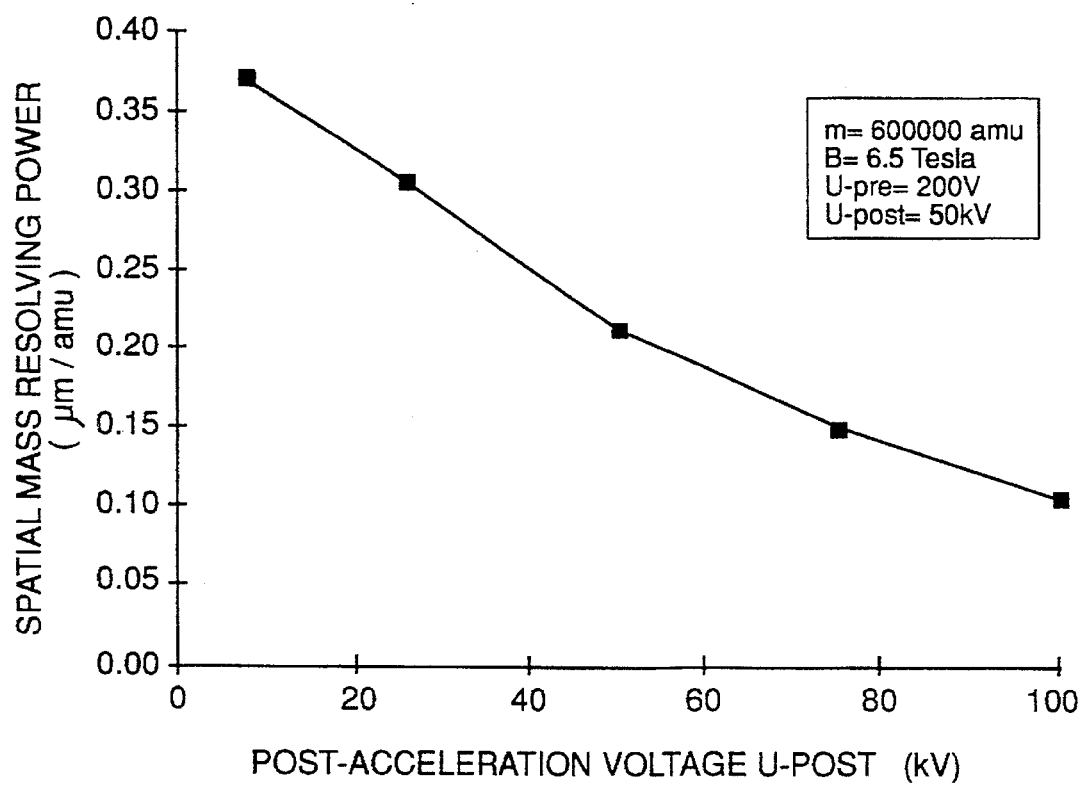
FIG. 12 shows the results of a calculation illustrating the dependence of the spatial mass resolving power versus post-acceleration voltage in the embodiment of FIG. 11.
Figure 13:
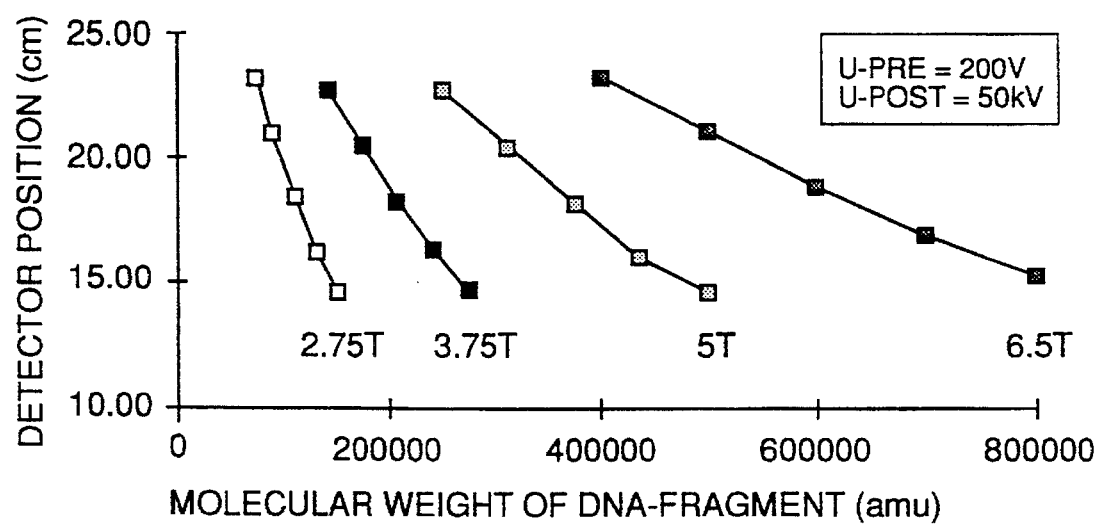
FIG. 13 shows the results of a calculation illustrating the dependence of the spatial mass separation versus molecular weight in the embodiment of FIG. 11.
Figure 14:
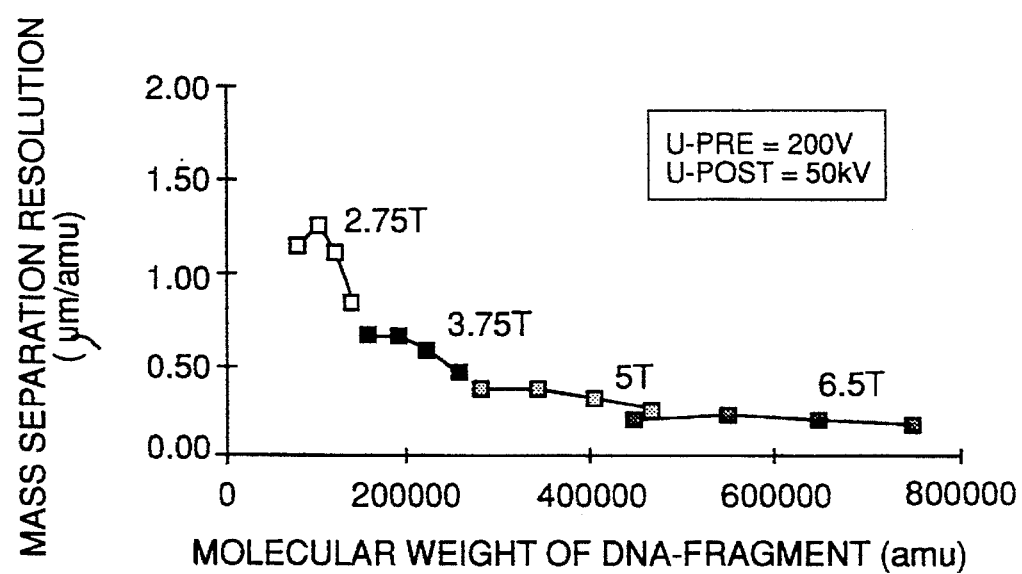
FIG. 14 shows the results of a calculation illustrating the dependence of the mass separation resolution versus molecular weight in the embodiment of FIG. 11.

The mass separation of the macromolecules is determined by the combination of the magnetic field strength B and the pre-acceleration voltage $U_{pre}$. A post-acceleration voltage $U_{post}$ is required to accelerate the macromolecules to a sufficiently high kinetic energy of a few 10 keV, in order to be detectable by the cryogenic detector array. Increasing $U_{post}$ will make detection of the macromolecules by the cryogenic detector array easier, but, as is apparent from FIG. 12, the macromolecules are then focussed to a smaller region of the cryogenic detector array, reducing the spatial mass resolving power accordingly. In FIG. 13 the various mass ranges for different values of the magnetic field strengths are shown. For a given magnetic field strength, the mass range of macromolecules reaching the cryogenic detector array is finite because of the finite exit window of the mass separator as shown in FIG. 10. As is apparent from FIG. 13, larger magnetic fields yield larger mass ranges which can be detected simultaneously by the cryogenic detector array. However, because those masses are spread out on a length of 10 cm, the spatial mass separation resolution decreases for increasing masses, as shown in FIG. 14. Magnetic fields of 6.5 T can be readily achieved with superconducting coils, however the relatively large area will be technologically challenging. A good homogeneity of the magnetic field is required, small inhomogeneities can be corrected for by considering the two important calibration curves of this preferred embodiment of the invention: the position calibration curve $M_{x-cal}(x)$ and the time calibration curve $M_{t-cal}(t)$. In order to obtain a good mass resolution, a short and long time stability of the magnetic field will be important.

Figure 15:
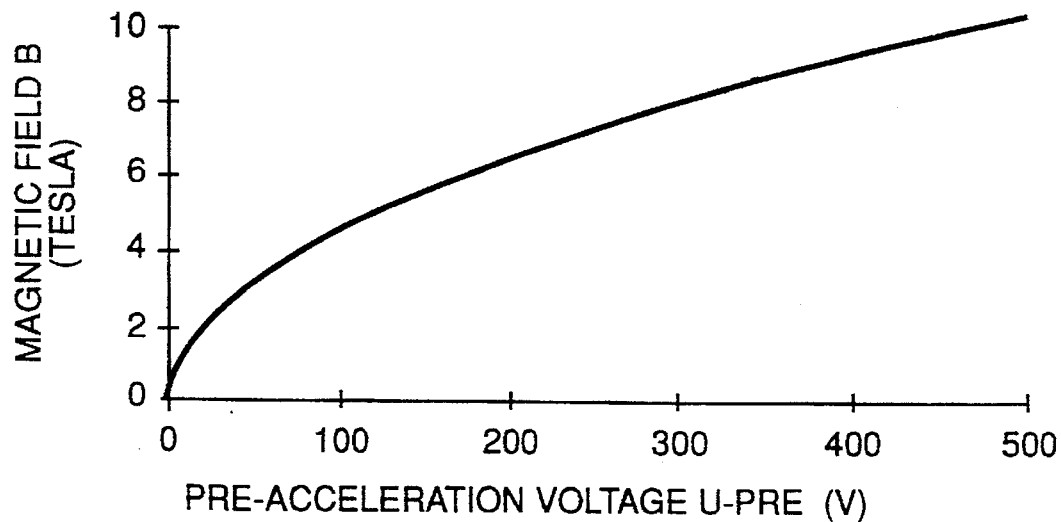
FIG. 15 shows the results of a calculation illustrating the dependence of the required magnetic field versus the required pre-acceleration voltage for detecting macromolecules in the embodiment of FIG. 11 in the mass range according to FIG. 10.
Figure 16:
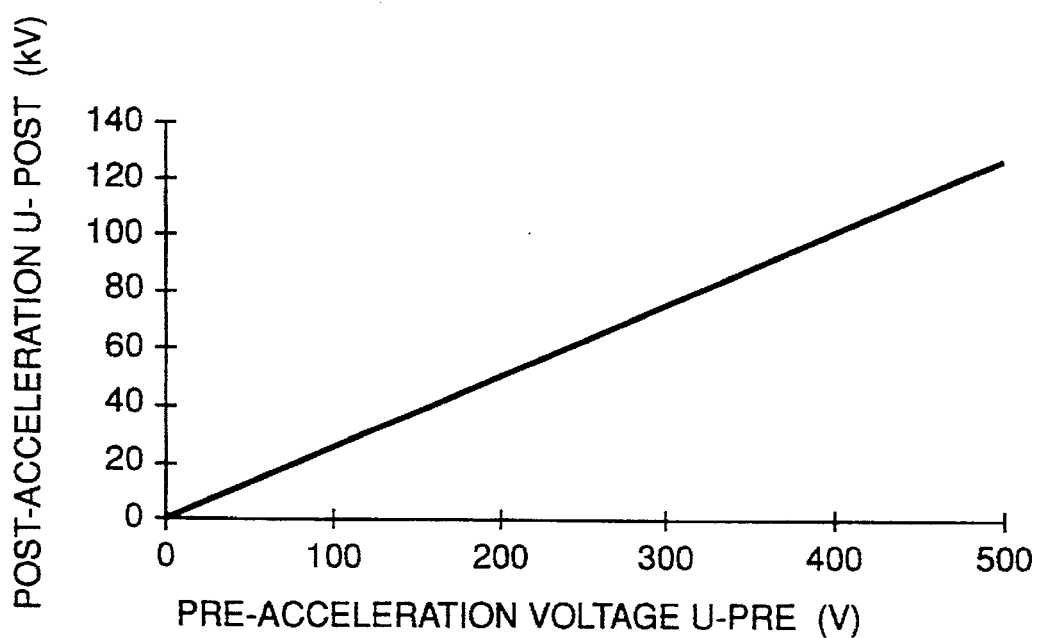
FIG. 16 shows the results of a calculation illustrating the dependence of the post-acceleration versus the required pre-acceleration voltage for detecting macromolecules in the embodiment of FIG. 11 in the mass range according to FIG. 10.

Another critical factor for achieving a good mass resolution with this high throughput mass spectrometer is the quality of the ionized macromolecular beam entering the mass separator (reference number 65 in FIG. 10). This beam will have to be highly collimated and should be manoener-getic. It is to be expected that this high beam quality would be achieved more easily for higher pre-acceleration voltages $U_{pre}$. The three operating parameters magnetic field B, $U_{pre}$ and $U_{post}$ cannot, however, be chosen independently for a given mass range. In FIG. 15 the required magnetic field strength B to detect the mass range between 400000 and 800000 amu at the position of the cryogenic detector array is given as a function of $U_{pre}$, and in FIG. 16 the corresponding post-acceleration value $U_{post}$ is given as a function of $U_{pre}$ for the same mass range. If, for instance, one selects a pre-acceleration voltage of 400 V, then the magnetic field would have to be set to a value of 8 Tesla (FIG. 15) and $U_{post}$ to a value of 100 kV (FIG. 16), in order to detect the mass range between 400000 and 800000 amu at the position of the cryogenic detector array. An advantage of this preferred embodiment of the invention is that within a fixed geometry, a mass range of macromolecules can be scanned for masses ranging from virtually zero to a mass limited only by the highest permissable magnetic field. In addition, the pre- and post-acceleration voltages can be chosen such to optimize the overall performance.

Figure 17:
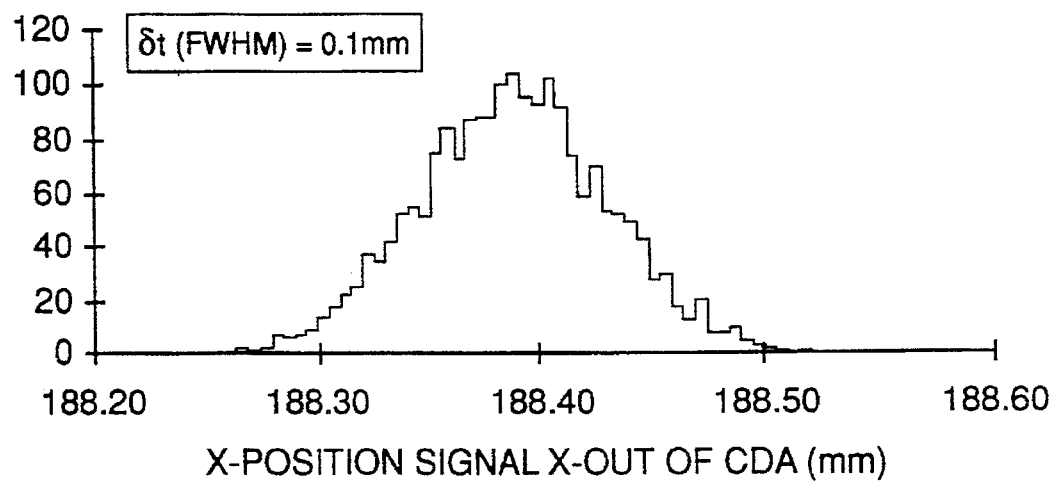
FIG. 17 shows the results of a Monte-Carlo calculation illustrating the position resolution of an embodiment of FIG. 7, FIG. 8 or FIG. 9 used in the embodiment of FIG. 11.
Figure 18:
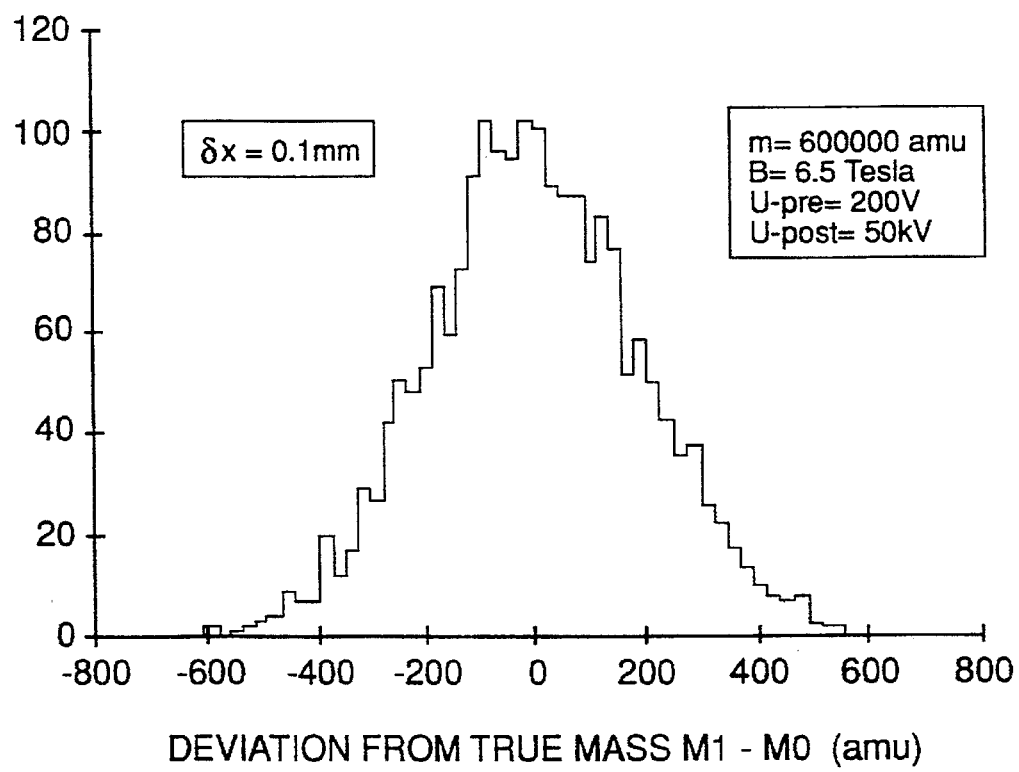
FIG. 18 shows the results of a Monte-Carlo calculation illustrating the reconstructed mass resolution as derived from FIG. 17.

The mass of the macromolecules can be directly determined from the spatial mass resolving power of the cryogenic detector array (see FIG. 14). In this particular numerical model, the spatial mass resolving power of the cryogenic detector array is 0.2 µm/amu (see FIG. 14). If one wants to realize a mass resolution of, say, 100 amu (which would required if one were to measure the mass of large DNA-fragments for DNA-sequencing, where the base mass is approximately 300 amu, see below) one would need a spatial resolution of the cryogenic detector array of 25 µm. This would require about 4000 individual detectors for a cryogenic detector array of 10 cm length in the embodiment shown in FIG. 7. When using the embodiment of a cryogenic detector array as shown in FIG. 8 or FIG. 9, one could obtain a spatial resolution δx=0.1 mm with phonon sensors spaced 1 mm apart. Then only 100 phonon sensors would be required to span the 10 cm. A monte-Carlo calculation was performed to investigate the mass resolution properties of the various embodiments of this invention. The "true" values $X_{stop}$ of 2000 macromolecules with a mass of $M_0$=600000 amu were randomized by a gaussian distribution with a FWHM (full width at half maximum) of δx=0.1 mm, simulating the cryogenic detector array output $x_{out}$. In FIG. 17 the spatial x-position signal distribution of the cryogenic detector array output $x_{out}$ is shown. With the calculated machine's calibration curve $M_{x-cal}(x)$, obtained by calculating the trajectories of the corresponding macromolecules, a mass $M_1$ was determined. In FIG. 18 the corresponding distribution of the mass error $M_1-M_0$ is shown. The FWHM of this mass error distribution is about 500 amu and would be insufficient for DNA-sequencing. However, this mass resolution can be improved by using a time-of-flight strategy and the embodiment of a pulsed emission mode of this high-throughput mass spectrometer. This will be the scope of the following section.

Figure 19:
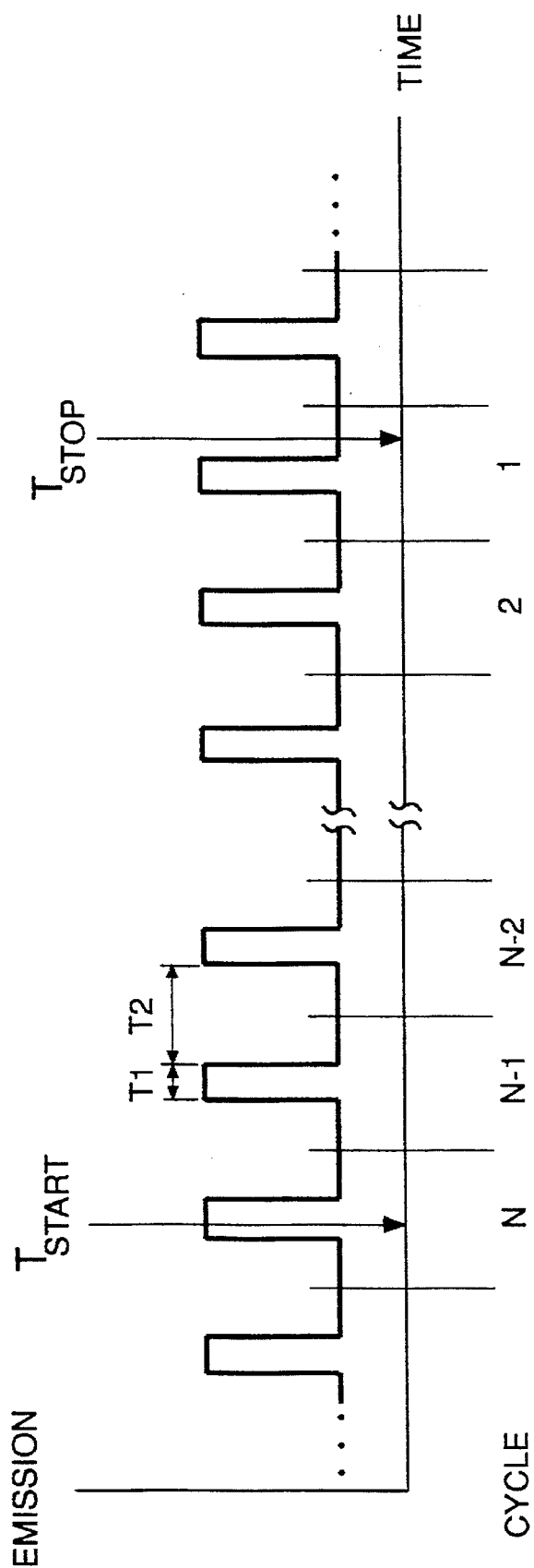
FIG. 19 illustrates the pulsed emission mode of the embodiment shown in FIG. 11.

In a time-of-flight mass spectrometer, one measures the time difference between the time of emission $t_{start}$ of a particle and its time of impact $t_{stop}$ at a given detector. As the typical time-of-flight of a macromolecule in our numerical model is 5 msec, one could emit a pulse of macromolecules every $T_2$=10 msec with a pulse length of, say, $T_1$=100 nsec. This would yield a duty cycle $T_1/(T_1+T_2)$ of $10^{-5}$, and accordingly a low throughput of the device. The idea of this particular embodiment of operating mode is to perform many time-of-flight measurements in parallel by profiting form the spatial separation of the trajectories in the magnetic field. The pulsed emission is shown in FIG. 10. The stop signal $t_{stop}$ is measured by the cryogenic detector array, but the starting time $t_{start}$ of the corresponding event remains to be determined. This is done by using the spatial separation of the trajectories as follows: As is shown in FIG. 19, the macromolecules are emitted in pulses with a pulse length $T_1$ and a non-emission pause $T_2$. Such an emission pulse can be achieved by a corresponding laser pulses in the MALDI scheme, or with switching the electro-optics in the pre-acceleration phase. With the knowledge of the two calibration curves of the proposed embodiment—the position calibration curve $M_{x-cal}(x)$ and the time calibration curve $M_{t-cal}(t)$—the mass of macromolecule can be reconstructed in the following way. The starting point are the two output signals of the cryogenic detector array:

$$x_{out}=x_{stop}+\delta x$$

$$t_{out}=t_{stop}+\delta t$$

where $x_{stop}$ is the true position of absorption and $t_{stop}$ the true time of impact at the cryogenic detector array, and δx and δt are deviations from the true values owing to the spatial and time resolution of the cryogenic detector array, respectively. From the value $x_{out}$ one determines a first guess $M_1$ of the mass by using the position calibration curve:

$$M_1=M_{x-cal}(x_{out})$$

Entering this value $M_1$ into the inverse $M_{t-cal}^{-1}$ of the time calibration curve one obtains a first guess $t_1$ of the emission time:

$$t_1=t_{out}-M_{t-cal}^{-1}(M_1)$$

Now, knowing that the macromolecule must have been emitted during one of the emission pulses, one can identify the corresponding cycle number N in which the macromolecule was emitted (see FIG. 19).

$$N=1+\frac{t_1}{T_1+T_2}$$

and obtain a better second guess $t_2$ of the emission time by identifying $t_{start}$ with the leading edge of the emission pulse:

$$t_2=(N-1)(T_1+T_2)+\frac{T_2}{2}$$

The value of $t_2$ is, of course, only known to a precision corresponding to the pulse length $T_1$. Using again the time calibration curve, one finally arrives at the TOF value $M_2$ of the mass:

$$M_2=M_{t-cal}(t_{out}-t_2)$$

Figure 20:
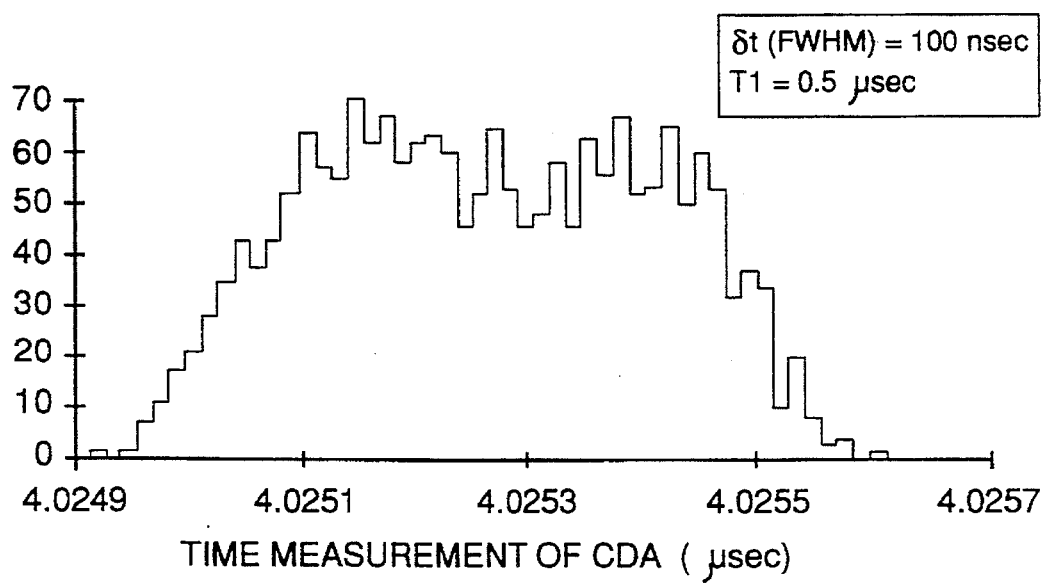
FIG. 20 shows the results of a Monte-Carlo calculation illustrating the arrival time resolution of an embodiment of FIG. 7.

In this TOF operating mode, the precision of the value $M_2$ of the macromolecule is determined by the length $T_1$ of the emission pulse and the time resolution δt of the cryogenic detector array. In this pulsed operating mode, the spatial resolution δx of the cryogenic detector array is only required for reconstructing the cycle number N and does not enter the mass resolution directly. In FIG. 20 the Monte Carlo distribution of the detector time-of-arrival signal $t_{stop}$ is shown for pulse width of $T_1$ of 0.5 µsec and a time resolution δt of the cryogenic detector array of 100 nsec.

Figure 21:
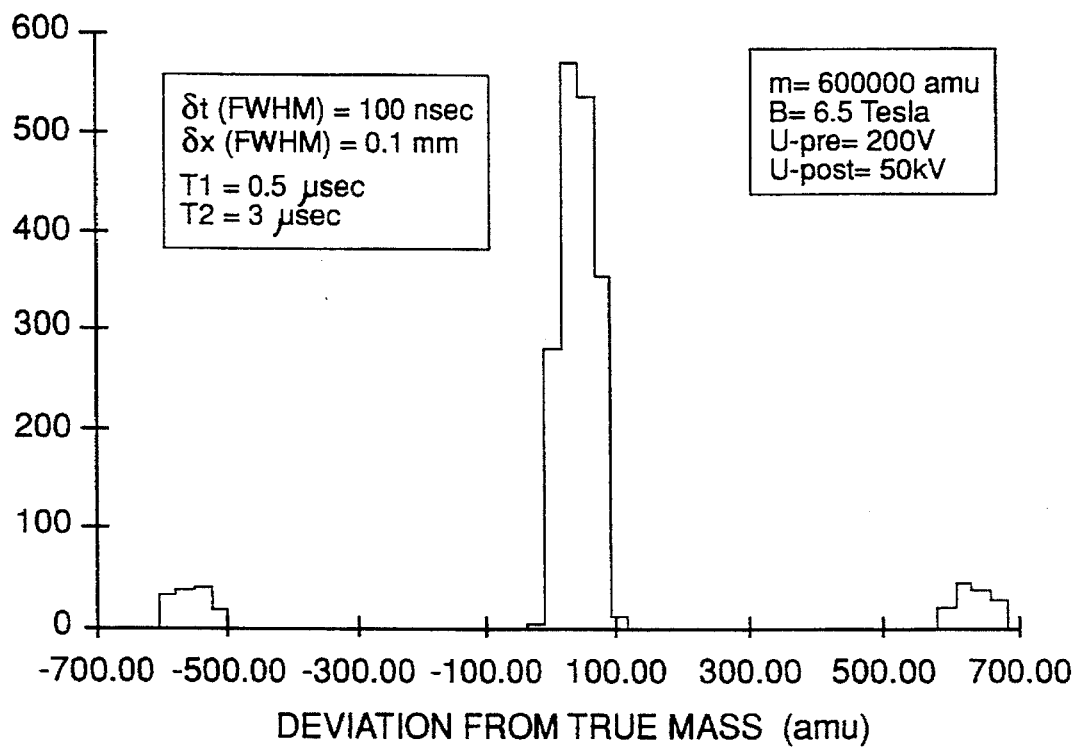
FIG. 21 shows the results of a Monte-Carlo calculation illustrating the reconstructed mass resolution as derived from FIG. 20.
Figure 22:
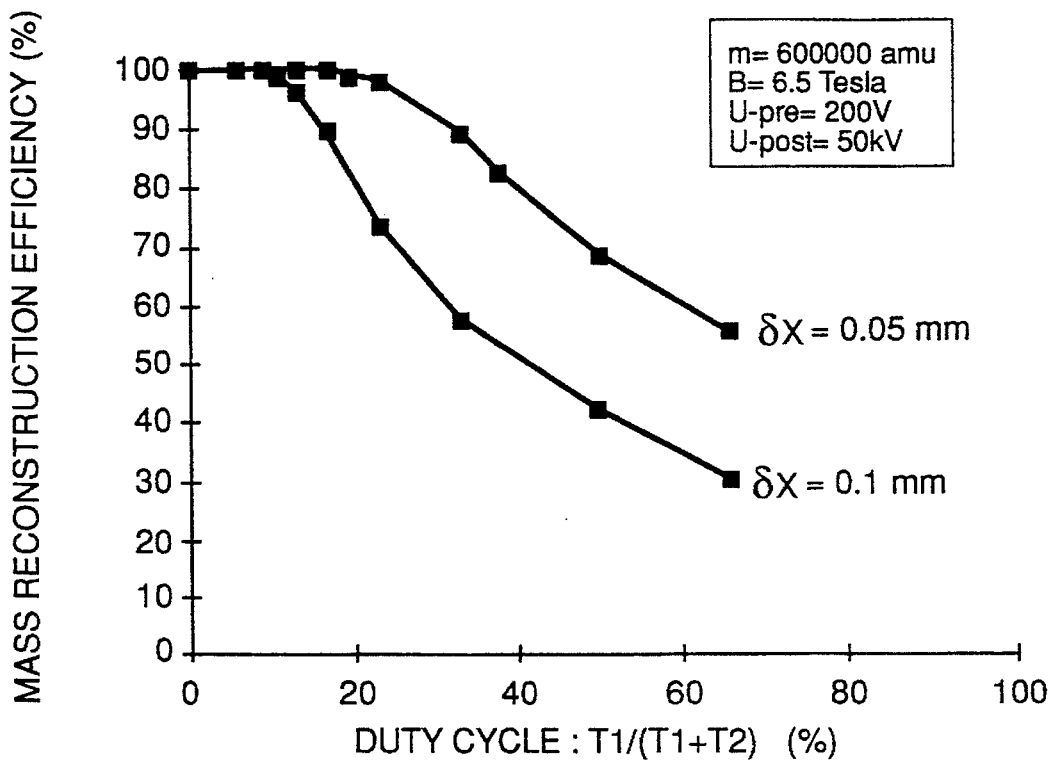
FIG. 22 shows the results of a calculation illustrating the dependence of the mass reconstruction efficiency versus the duty cycle in the pulsed emission operating mode as shown in FIG. 19 in the embodiment as shown in FIG. 11.

In FIG. 21, the distribution of the TOF reconstructed mass is shown, which was obtained as follows: in the Monte Carlo calculation, each event was characterized by its corresponding value $x_{out}$ (FIG. 17) and $t_{stop}$ (FIG. 20). Using the mass reconstruction described above, the mass value $M_2$ was determined by entering those two variables into the corresponding calibration curves. The distribution of the mass determination error $M_2-M_0$ has a central peak with a FWHM of 100 amu corresponding to correctly identified cycle numbers N and two side peaks with the same FWHM corresponding to falsely identified neighbouring emission cycles owing to a "leakage" of values of $t_1$ into those emission cycles (see FIG. 19). The reason for this "leakage" is the limited spatial resolution δx of the cryogenic detector array and the correspondingly small value $T_2$ of the pause in the pulse sequence. Increasing $T_2$ for a given value of δx reduces the number of erraneously constructed events. However, the duty cycle will then be reduced accordingly. In FIG. 22, the calculated mass reconstruction efficiency is shown as a function of duty cycle for two values of spatial resolution δx, where the mass reconstruction efficiency is defined to be the ratio of correctly to uncorrectly reconstructed events.

Figure 23:
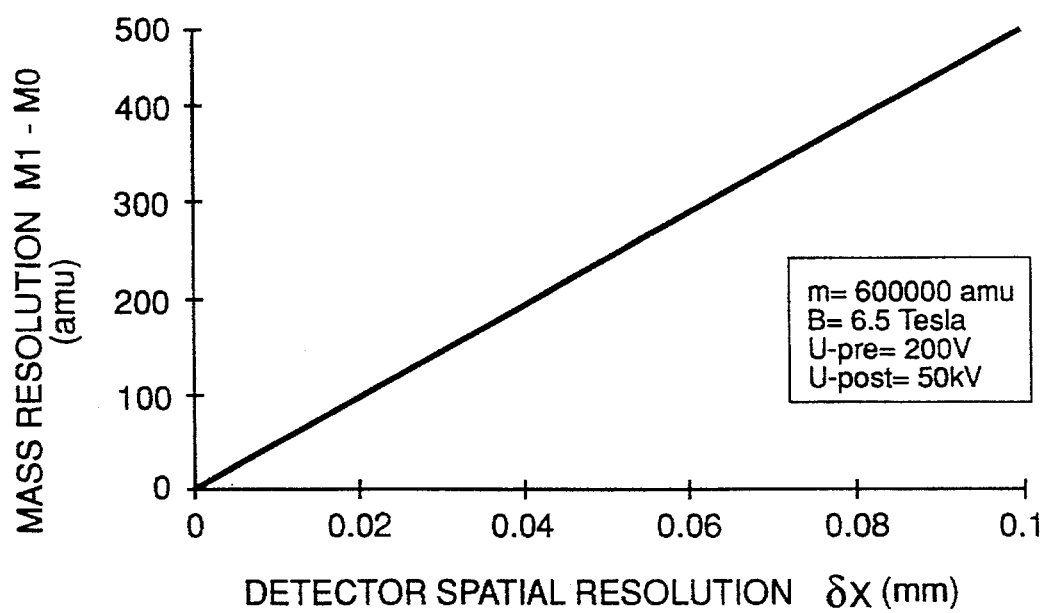
FIG. 23 shows the results of a calculation illustrating the dependence of the mass resolution as derived from the spatial resolution of the cryogenic detector array verses the spatial resolution of the cryogenic detector array in the embodiment as shown in FIG. 11.
Figure 24:
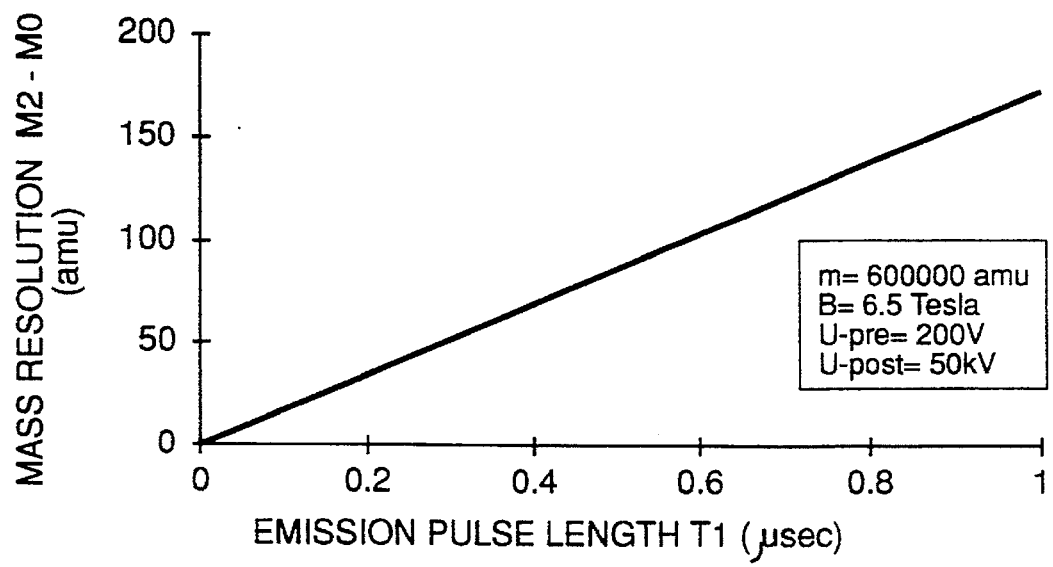
FIG. 24 shows the result of a calculation illustrating the dependence of the mass resolution as derived from the time-of-flight when using the the pulsed emission operating mode as shown in FIG. 19 versus the emission pulse length in the embodiment as shown in FIG. 11.

The mass resolution of the directly measured mass value $M_1$ can be improved by increasing the spatial resolution of the cryogenic detector array (i.e. by making the corresponding value of $\delta$ smaller), as is shown in FIG. 23. The corresponding mass resolution of the TOF deduced mass distribution $M_2$ can be improved by reducing the emission pulse length $T_1$, as shown in FIG. 24. However, in the latter case the mass resolution will be more likely be determined by the finite time resolution of the cryogenic detector array. The calculated mass resolutions above were obtained under the assumption that the ionized, pre-accelerated beam of macromolecules enters the mass seperator perfectly collimated, with all macromolecules having the same kinetic energy of 200 eV. This, of course, will not be true in a real device, and it will be one of the main technological challenges in constructing this preferred embodiment of the invention to fulfill those ideal initial beam conditions as much as possible.

A particular use of this preferred embodiment of the invention is for high throughput DNA-sequencing. The goal of DNA-sequencing is to determine the sequence of the four bases making up the DNA alphabet, A (adenine), G (guanine), T (thymine) and C (cytosine). In the molecular biology laboratory, aliquots containing DNA-sequence ladders are prepared according to either the Sanger or the Maxam-Gilbert. Taking the Sanger strategy as example, four aliquots of the same part of the DNA are produced which can be labeled by the four bases A, G, T and C, each aliquot containing information on the corresponding base position in the specific part of DNA in question. Conventionally, the macromolecules are sorted according to their length for each of the four aliquots by using the technique of gel-electrophoresis. There, the macromolecules migrate in a gel which is placed in an electric field. For a given duration, the shorter fragments migrate farther than the longer fragments, leading to a separation of the macromolecules accordingly. The major disadvantage of gel-electrophoresis is the long time (of the order of hours) required for the macromolecules to migrate through the gel. Typically a good equipped laboratory can sequence of the order of 10000 bases per day.

Figure 25:
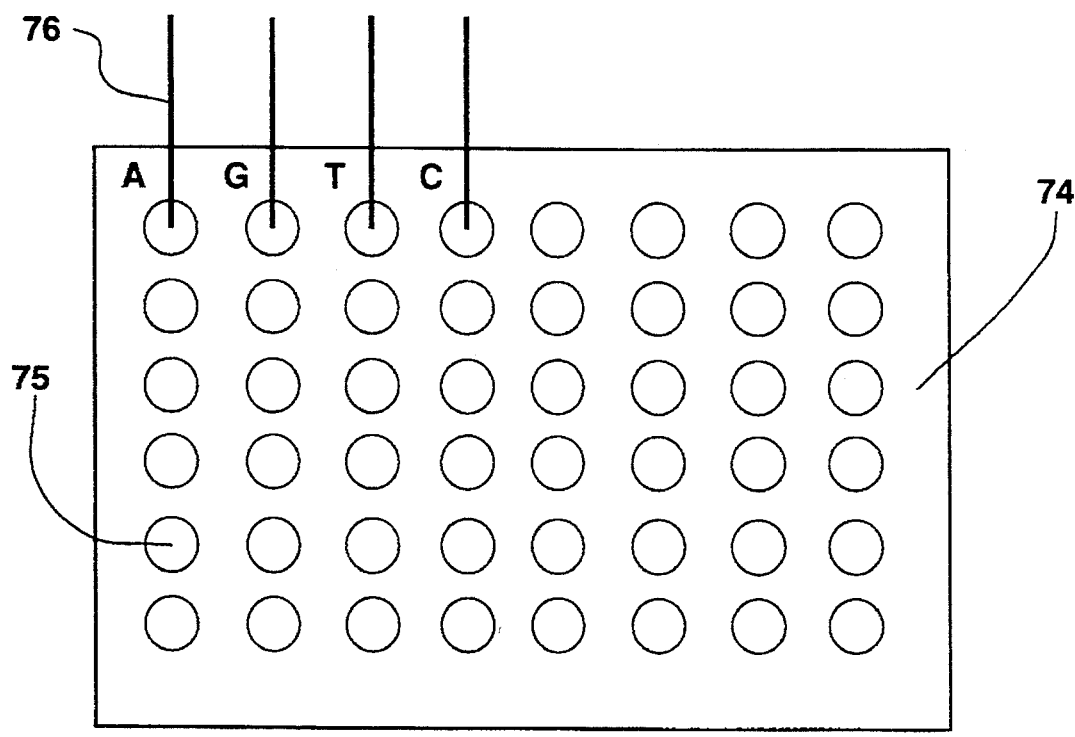
FIG. 25 is a schematic of an embodiment of a probe sample used for DNA-sequencing in the embodiment as shown in FIG. 11.

An intrinsically much faster method is to separate the DNA-fragments according to their masses by using mass spectrometry. As has been shown above, in the preferred embodiment of this invention, large DNA-fragments of mass 600000 amu can be analyzed with a mass resolution of the order of 100 amu. In the following, the rate of analyzing the aliquots of the equivalent of the human genome consisting of $3 \cdot 10^9$ bases is estimated for this preferred embodiment. Because of the single particle counting property of the cryogenic detector array, pile-up has to be prevented. One has, hence, to assure that only a small number of macromolecules will reach the detector array at any given time. Then the single particle counting property of the cryogenic particle detector will allow a one-to-one identification of each set of detector values $(x_{stop}, t_{stop})$ to a unique emission cycle of the pulsed emission. Although heavier molecules from an earlier emission event will arrive the cryogenic detector array later than a lighter molecule from a later emission event, they will never reach the same position of the detector, because each trajectory is unique for each mass/charge ratio. It is one advantage of this preferred embodiment that multiple charged macromolecules can be distinguished by their different response to the operating parameters. If one places the DNA-fragment aliquots to be analyzed on a chip as illustrated in FIG. 25, the emission of each aliquot can be synchronized to the emission pulse of the mass spectrometer. Each mass value measured by the cryogenic detector array can then be correlated to a specific aliquot on the chip. We again take the mass range of the spectrometer to be between 400000 amu and 800000 amu and assume the mass resolution to be sufficient to separate bases, i.e. $\Delta m < 300$ amu. Because of the finite resolution of the system, we assume that 100 events are required per macromolecule to unambiguously identify its mass. Within this given mass range, a sequencing ladder consisting of 1300 bases can be reconstructed for the four aliquots denoted by A, G, T and C in FIG. 25. In order to reconstruct successfully the mass from the detector values $(x_{stop}, t_{stop})$, and to correlate the macromolecule to the aliquot on the chip it originated from, only one macromolecule should hit in average the detector at a given position and time for no pile-up to occur. A given aliquot would therefore have to be analyzed a 100 times. If the emission pulse period is chosen to be 100 µsec, then one can reconstruct the sequence of the 1300 bases of the given DNA-strand in $100 \times 4 \times 100$ µsec=40 msec. The next four aliquots would correspond to macromolecule populations shifted by 1300 bases. Again it would take 40 msec for those 1300 bases to be sequenced. In one second the machine would therefore be capable to reconstruct $3.25 \cdot 10^4$ bases, or, in other words, the equivalent number of bases of the entire human genome consisting of $3 \cdot 10^9$ bases could be sequenced in $9.2 \cdot 10^4$ seconds, i.e. in 25 hours. If one were to sequence the human genome with one single gel-electrophoresis apparatus capable of sequencing 10000 bases a day, it would take 800 years in comparison. However, the separation of the sequence ladder is only one of the steps required in DNA-sequencing. The biochemical production of the sequence ladder is elaborate and will require much more than a few hours for the entire human genome. Nevertheless, sample arrays can be prepared and stored as indicated in FIG. 25 by different laboratories in parallel and analyzed by the preferred embodiment of this invention in a very short time.

The entire amount of DNA required is also small: a sample array as shown in FIG. 25 would have to consist of $3 \cdot 10^9 / 1300 = 2.3 \cdot 10^6$ aliquots, which can be put in the form of an array of $1500 \times 1500$ aliquots. In our example, the four aliquots designated by A,G,T and C together contain the complete ladder of 1300 macromolecules with an average mass of 600000 amu. The total mass of macromolecules hitting the cryogenic detector array per emission cycle (i.e. per aliquot) is therefore $(1300/4) \times 600000$ amu. Because one has to analyze the same aliquot a 100 times to get a good estimate for the mass this value has to be multiplied by 100. In addition, because the overall volatilizing and ionizing efficiency is probably not better than $10^{-4}$, the amount would have again to be multiplied by a factor of $10^4$. Per aliquot we therefore obtain (1 amu=$1.66 \cdot 10^{-24}$ g):

amount of DNA per aliquot =

$$10^4 \cdot 100 \cdot \frac{1300}{4} \cdot 600000 \text{ amu} = 0.32 \cdot 10^{-9} \text{ g}$$

Multiplying by the number of aliquots on the sample array ($2.3 \cdot 10^6$) one gets for the total amount of DNA required on the sample array:

total amount of DNA on sample array=$2.3 \cdot 10^6 \times 0.32 \cdot 10^{-9}$ g=$0.74 \cdot 10^{-3}$ g Now let us estimate the size of the sample array: As each aliquot consists basically of a solvent with the DNA dissolved to a factor of $10^{-4}$, the mass of a aliquot would be $3.2 \cdot 10^{-6}$ g. If, for simplicity, we assume the density to be the density of water, this mass would correspond to a volume of $3.2 \cdot 10^{-6}$ cm$^3$, or, alternatively to a aliquot radius of 91 μm. The aliquots could therefore be spaced at a distance of 0.2 mm each. The overall size of the sample array would hence be:

sample array size=(1500·0.2 mm)×(1500·0.2 mm)=30 cm×30 cm

The total amount of DNA accumulated on the cryogenic detector array during the sequencing of the entire humane genome as described above would be $7.4 \cdot 10^{-10}$ g, which corresponds to a film thickness of 7.4 nm for a cryogenic detector array of 10 cm length and a molecular beam height of 1 mm. A polymer film of this thickness will hardly alter the phonon sensitivity of the cryogenic detector.

In the calculations presented above, DNA-sequencing was as an application of the preferred embodiment of the invention. It goes without saying that the description above also apply for proteins, peptides, polymers or any other macromolecule.

While the forms of the invention herein constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

REFERENCES

1. M. Barber et al., Anal. Chem., 54 (1982) 645 A.
2. J. E. Bruce et al., Rapid Commun. Mass Spectrom., 7 (1993) 914.
3. S. M. Michael et al., Anal. Chem. 65 (1993) 2614.
4. M. Karas and F. Hillenkamp, Anal. Chem. 60 (1988) 2299.
5. R. T. Melver et al., Int. J. Mass Spectrom. Ion Processes, 132 (1994) L1.
6. J. A. Castoro and C. L. Wilkins, Anal. Chem. 65 (1993) 2621.
7. K. J. Wu et al., Rapid Commun. Mass Spectrom., 7 (1993) 142.
8. P. Williams, Int. J. Mass Spectrom. Ion Processes, 131 (1994) 335.
9. D. F. Hunt et al., Proc. Natl. Acad. Sci. U.S.A. 83 (1986) 6233.
10. A. L. Cox et al., Science 264 (1994) 716.
11. J. Linhard and M. Scharf, Phys. Rev., 124 (1961) 128.
12. M. W. Senko and F. W. McLafferty, Annu. Rev. Biophys. Biomol. Struct. 23 (1994) 763.
13. Q. Xie, Science 256 (1992) 225.
14. "Advances in DNA Sequencing Technology", R. A. Keller (ed.), SPIE 1891, (1993).
15. D. C. Schwartz and C. R. Cantor, Cell 37 (1984) 67.
16. M. Burmeister and L. Ulanovsky (ed.) Methods in Molecular Biology, Vol 12, "Pulsed-Field Gel Electrophoresis" (1992).
17. D. Twerenbold, Europhys.Lett., 1 (1986) 209.
18. H. Kraus et al., Europhys.Lett., 1 (1986) 161.
19. Proceedings of the 5. International Workshop on Low Temperature Detectors, University of California at Berkeley, Jul. 29–Aug. 3, 1993. Special issue: Journal of Low Temperature Physics 93 (1993).
20. D. Twerenbold, Phys. Rev B., 34 (1986) 7748.
21. Y. DeCoulon, D. Twerenbold and J.-L. Vuilleumier, Nucl. Instr. and Meth., A294 (1990) 259.
22. N. E. Booth, Appl. Phys. Lett., 50 (1987) 293.
23. The calculations of the potential field lines and trajectories are based on the POISSON group of codes developed by R. Holsinger and K. Halbach of the Los Alamos National Laboratory.

What is claimed is:

1. A mass spectrometer comprising:

means for volatilizing and charging macromolecules out of a condensed solution;

an evacuated receptacle in which said macromolecules are volatilized and charged by said means;

electro-optical means placed in said receptacle for accelerating said charged macromolecules;

a high voltage power supply and electrical connected to said electro-optical means;

an evacuated receptacle of sufficient length for separating said accelerated macromolecules by their different velocities;

a phonon sensitive cryogenic particle detector consisting of an absorber and one or more phonon sensors for detecting the time of impact of said accelerated macromolecules; whereby said macromolecules excite phonons in said absorber and whereby said phonon sensors convert said phonons into an electronic signal;

a mechanical shutter consisting of a rotating disk for preventing low mass molecules from hitting said cryogenic particle detector;

a preamplifier system for converting the detector signal of said cryogenic particle detector into a low impedance signal for further data processing;

a cryostat with a cold finger to which said cryogenic detector is thermally connected.

2. A mass spectrometer comprising:

means for volatilizing and charging macromolecules out of a condensed solution;

a first evacuated receptacle in which said macromolecules are volatilized and charged by said means;

electro-optical means placed in said first receptacle for pre-accelerating said charged macro-molecules;

a first high voltage power supply and electrical connected to said electro-optical means;

a magnet for generating a magnetic field of constant strength and high homogeneity over a predetermined space;

a current power supply and electrical connected to said magnet for generating said magnetic field;

a second evacuated receptacle connected to said first receptacle via a feed through and placed inside said magnet, but electrically insulated from said magnet, in which said charged macromolecules move on trajectories determined by their mass-to-charge ratio;

a third evacuated receptacle with a feed through to said second evacuated receptacle in which said charged macromolecules are accelerated after having been separated in said magnet by their mass-to-charge ratios;

a second high voltage power supply and electrical connected to said three receptacles for accelerating said charged macromolecules;

a phonon sensitive cryogenic detector array consisting of a cryogenic particle detector with one or more absorbers and one or more arrays of phonon sensors for detecting the time of impact and the position of impact of said accelerated macromolecules; whereby said macromolecules excite phonons in said absorber and whereby said phonon sensors convert said phonons into an electronic signal;

a preamplifier system for converting the detector signal of said cryogenic detector array into a low impedance signal for further data processing;

a cryostat with a cold finger to which said cryogenic detector array is thermally connected;

a magnetic shield to protect said cryogenic detector array from the stray magnetic fields of said magnet.

3. A mass spectrometer comprising:

means for volatilizing and charging macromolecules out of a condensed solution;

an evacuated receptacle in which said macromolecules are volatilized and charged by said means;

electro-optical means placed in said receptacle for accelerating said charged macromolecules;

a high voltage power supply and electrical connected to said electro-optical means;

an evacuated receptacle of sufficient length placed in one or more quadrupole mass filters for selecting specified masses of said macromolecules;

a phonon sensitive cryogenic particle detector consisting of an absorber and one or more phonon sensors for detecting the time of impact of said accelerated macromolecules; whereby said macromolecules excite phonons in said absorber and whereby said phonon sensors convert said phonons into an electronic signal;

a preamplifier system for converting the detector signal of said cryogenic particle detector into a low impedance signal for further data processing;

a cryostat with a cold finger to which said cryogenic detector array is thermally connected.

4. A mass spectrometer according to claims 1 through 3, wherein said absober and said phonon sensor of said cryogenic particle detector are identical and wherein said excited phonons are directly converted into an electronic signal.

5. A mass spectrometer according to claims 1 through 3, wherein said absorber of the cryogenic particle detector is single crystal silicon.

6. A mass spectrometer according to claims 1 through 3, wherein said absorber is single crystal sapphire.

7. A mass spectrometer according to claims 1 through 3, wherein said absorber is single crystal germanium.

8. A mass spectrometer according to claims 1-3, wherein said phonon sensors are superconducting tunneling junctions operated in the Giaever-mode; whereby said excited phonons break Cooper pairs in the superconducting films of said superconducting tunneling junctions and produce excess quasiparticles; whereby said excess quasiparticles tunnel through a insulating barrier of said superconducting tunneling junctions and produce and excess quasiparticle current which constitutes said electronic signal; whereby a magnet field is applied parallel to the superconducting tunneling junctions by a magnet in order to suppress the DC Josephson current.

9. A mass spectrometer according to claim 8, wherein said superconducting tunneling junctions are deposited on top of large area superconducting films with a superconducting energy gap larger than the corresponding superconducting energy gap of said superconducting tunneling junctions; whereby said excess phonons first travel into said large area superconducting films where they break Cooper pairs and produce said excess quasiparticles which are trapped in said superconducting tunneling junctions.

10. A mass spectrometer according to claim 8, wherein said superconducting structures are of niobium or an alloy of niobium.

11. A mass spectrometer according to claim 8, wherein said superconducting structures are of tantalum or an alloy of tantalum.

12. A mass spectrometer according to claim 8, wherein said superconducting structures are of tin or an alloy of tin.

13. A mass spectrometer according to claim 8, wherein said superconducting structures are of indium or an alloy of indium.

14. A mass spectrometer according to claim 8, wherein said superconducting structures are of lead or an alloy of lead.

15. A mass spectrometer according to claims 1-3, wherein said phonon sensors are superconducting transition edge thermometers; whereby said superconducting transition edge thermometers are operated at temperatures close to their phase transition temperature and biased electrically with a current slightly below their critical current; whereby said superconducting transition edge thermometers are heated due to said excess phonons; whereby said heating produces a temperature rise; whereby said temperature rise produces a superconducting to normal phase transition; whereby said phase transition produces a voltage signal which constitutes said electronic signal.

16. A mass spectrometer according to claim 15, wherein said superconducting structures are of aluminum or an alloy of aluminum.

17. A mass spectrometer according to claim 15, wherein said superconducting transition edge thermometer consist of iridium/gold layers.

18. A mass spectrometer according to claims 1-3, wherein said phonon sensors are superconducting kinetic inductance thermometers; whereby said superconducting kinetic inductance thermometers are operated at temperatures close to their phase transition temperature and biased electrically with a current slightly below their critical current; whereby said superconducting kinetic inductance thermometers are heated up due to said excess phonons; whereby said heating produces a temperature rise; whereby said temperature rise produces a change in the London penetration depth; whereby said change in the London penetration depth produces a change in the inductance of the electronic circuitry; whereby said change in inductance produces a voltage signal which constitutes said electronic signal.

19. A mass spectrometer according to claims 1-3, wherein said phonon sensors are superconducting superheated granules; whereby said superconducting superheated granules are operated at temperatures close to their phase transition temperature; whereby the superconducting superheated granules are placed in an external magnetic field with a value slightly less than the critical magnetic field of said superconducting superheated granules; whereby said superconducting superheated granules are heated up due to said excess phonons; whereby said heating produces a temperature rise; whereby said temperature rise produces a superconducting to normal phase transition; whereby said phase transition produces a magnetic flux change owing to the penetration of magnetic field lines in the normal conducting granule; whereby said magnetic flux change produces a voltage signal in a pick up loop which constitutes said electronic signal.

20. A mass spectrometer according to claim 19, wherein said superconducting superheated granules act as said absorbers and said phonon sensors.

21. A mass spectrometer according to claim 19, wherein said superconducting superheated granules consist of small grains in a dielectric suspension.

22. A mass spectrometer according to claim 19, wherein said superconducting superheated granules consist of two dimensional structures deposited onto a substrate.

23. A mass spectrometer according to claims 1–3, wherein said phonon sensors consist of semiconducting thermistors; whereby said semiconducting thermistors are biased by an electrical current; whereby said excess phonons heat the absorber; whereby said heating up leads to a temperature rise; whereby said temperature rise leads to a change in resistance of the semiconducting thermistor; whereby said temperature rise produces a voltage signal which constitutes said electronic signal.

24. A mass spectrometer according to claims 1–3, wherein said pre-amplifier is integrated onto a substrate of said cryogenic particle detector.

25. A mass spectrometer according to claim 24, wherein said integrated pre-amplifier consists of superconducting structures.

26. A mass spectrometer according to claims 1–3, wherein said means for volatilizing and charging macromolecules out of a condensed solution is based on the Matrix-Assisted Laser Desorption/Ionization (MALDI) technique.

27. A mass spectrometer according to claims 1–3, wherein said means for volatilizing and charging macromolecules out of a condensed solution is based on the Electron Spray Ionization (ESI) technique.

28. A mass spectrometer according to claims 1–3, wherein said means for volatilizing and charging macromolecules out of a condensed solution is based on the Fast Atom Bombardment (FAB) technique.

29. A mass spectrometer according to claims 1–3, wherein said means for volatilizing and charging macromolecules out of a condensed solution is based on the Plasma Desorption (PD) technique.

30. A mass spectrometer according to claims 1–3, wherein said means for volatilizing and charging macromolecules out of a condensed solution is based on the Surface-Enhanced Neat Desorption (SEND) technique.

31. A mass spectrometer according to claims 1–3, wherein said means for volatilizing and charging macromolecules out of a condensed solution is based on volatilizing said macromolecules by thermal heating of a substrate on which said macromolecules are deposited; whereby said volatile macromolecules are charged by separate means.

32. A mass spectrometer according to claim 31, wherein said means for volatilizing the macromolecules by thermal heating is produced by high frequency phonon emission techniques.

33. A mass spectrometer according to claim 31, wherein said means for charging said volatile macromolecule is by photo ionization.

34. A mass spectrometer according to claim 31, wherein said means for charging said volatile macromolecule is by x-ray ionization.

35. A mass spectrometer according to claims 1–3, wherein the macromolecule has aliquots on a two dimensional sample array.

36. A mass spectrometer according to claims 1–3, wherein said mass spectrometer determines the mass of DNA-fragments for DNA-sequencing.

37. A mass spectrometer according to claims 1–3, wherein said mass spectrometer determines the mass of proteins or protein-fragments for protein-sequencing.

38. A mass spectrometer according to claims 1–3, wherein said mass spectrometer determines the mass of proteins or protein-fragments for protein-identification.

39. A mass spectrometer according to claims 1–3, wherein said mass spectrometer determines the mass of polymers or polymers-fragments for polymer identification.

40. A mass spectrometer according to claim 2, wherein said magnet is a superconducting magnet.

41. A mass spectrometer according to claim 2, whereby said mass spectrometer is operated in a pulsed operation mode; whereby said position of impact yields a first guess of the mass of said macromolecule; whereby said first guess of the mass together with said time of impact yields the time of emission of said macromolecule; whereby said first guess of time of emission and said time of impact yields a second, more precise, determination of the mass of said macromolecules by calculating the time difference of said time of impact and said time of emission.

42. A mass spectrometer consisting of a magnet, a mass separation receptacle in the magnetic field, a feed through and a detector system wherein the detector system consists of a phonon sensitive cryogenic detector system, the mass separation receptacle and the feed through are on a potential U1, which is different from the potential U2 of the detector system and, the region between the feed through and the detector system is shielded from the magnetic field of the magnet by a magnetic shield.

* * * * *

UNITED STATES PATENT AND TRADEMARK OFFICE
CERTIFICATE OF CORRECTION

PATENT NO. : 5,640,010
DATED : June 17, 1997
INVENTOR(S) : Damian Twerenbold

It is certified that error appears in the above-identified patent and that said Letters Patent is hereby corrected as shown below:

Title page,
Item [30], Foreign Application Priority Data, please delete the date "August 4, 2004" and insert therein -- August 3, 2004 --.

Signed and Sealed this

Fourteenth Day of September, 2004

JON W. DUDAS
*Director of the United States Patent and Trademark Office*